(12) United States Patent
Ledet et al.

(10) Patent No.: US 9,788,864 B2
(45) Date of Patent: Oct. 17, 2017

(54) DYNAMIC SPINAL FIXATION SYSTEM, METHOD OF USE, AND SPINAL FIXATION SYSTEM ATTACHMENT PORTIONS

(71) Applicant: REVIVO MEDICAL, LLC, Schenectady, NY (US)

(72) Inventors: Eric H. Ledet, Schenectady, NY (US); Glenn Patrick Sanders, Sand Lake, NY (US)

(73) Assignee: REVIVO MEDICAL, LLC, Schenectady, NY (US)

( * ) Notice: Subject to any disclaimer, the term of this patent is extended or adjusted under 35 U.S.C. 154(b) by 0 days.

(21) Appl. No.: 15/337,253

(22) Filed: Oct. 28, 2016

(65) Prior Publication Data
US 2017/0042583 A1    Feb. 16, 2017

Related U.S. Application Data

(63) Continuation of application No. 14/237,733, filed as application No. PCT/US2012/049959 on Aug. 8, 2012, now Pat. No. 9,510,871.
(Continued)

(51) Int. Cl.
*A61B 17/70* (2006.01)
*A61F 2/44* (2006.01)
(Continued)

(52) U.S. Cl.
CPC ...... *A61B 17/7026* (2013.01); *A61B 17/7007* (2013.01); *A61B 17/7011* (2013.01);
(Continued)

(58) Field of Classification Search
CPC ............ A61B 17/7062; A61B 17/7067; A61B 17/7068
(Continued)

(56) References Cited

U.S. PATENT DOCUMENTS

| 6,293,949 B1 * | 9/2001 | Justis | A61B 17/7011 606/279 |
| 7,666,185 B2 * | 2/2010 | Ryan | A61B 17/7059 606/71 |

(Continued)

OTHER PUBLICATIONS

International Search Report for PCT/US2012/049959 dated Jan. 17, 2013.
(Continued)

*Primary Examiner* — Ellen C Hammond
*Assistant Examiner* — Christina Negrellirodrigue
(74) *Attorney, Agent, or Firm* — Heslin Rothenberg Farley & Mesiti P.C.; Jacquelyn A. Graff

(57) ABSTRACT

Spinal fixation systems including a member, a first attachment portion, a second attachment portion, and an intermediate portion. The first attachment portion is attached at a superior end of the member and includes a first opening. The second attachment portion is attached at an inferior end of the member and includes a second opening. The intermediate portion connects the first and second attachment portions. The spinal fixation systems may also include a relief in at least one of the first opening and the second opening. The systems may also include a third attachment portion with a third opening and an intermediate portion with a first and a second elastic mechanism. The first elastic mechanism connects the first and third attachment portions and the second elastic mechanism connects the third and second attachment portions. Surgical methods for inserting the spinal fixation systems in a patient are also disclosed.

19 Claims, 23 Drawing Sheets

Related U.S. Application Data

(60) Provisional application No. 61/628,663, filed on Nov. 4, 2011, provisional application No. 61/628,662, filed on Nov. 4, 2011, provisional application No. 61/574,662, filed on Aug. 8, 2011, provisional application No. 61/574,636, filed on Aug. 8, 2011.

(51) Int. Cl.
  *A61B 17/80* (2006.01)
  *A61B 17/00* (2006.01)

(52) U.S. Cl.
  CPC ...... *A61B 17/7029* (2013.01); *A61B 17/7059* (2013.01); *A61F 2/4455* (2013.01); *A61B 17/701* (2013.01); *A61B 17/7004* (2013.01); *A61B 17/7025* (2013.01); *A61B 17/7028* (2013.01); *A61B 17/8023* (2013.01); *A61B 2017/00004* (2013.01)

(58) Field of Classification Search
  USPC ............ 606/246–249, 257; 623/17.11–17.16
  See application file for complete search history.

(56) References Cited

U.S. PATENT DOCUMENTS

| | | |
|---|---|---|
| 2004/0073215 A1 | 4/2004 | Carli |
| 2004/0087951 A1 | 5/2004 | Khalili |
| 2006/0229608 A1 | 10/2006 | Foster et al. |
| 2007/0233117 A1 | 10/2007 | Butler et al. |
| 2008/0108998 A1 | 5/2008 | Lindemann |
| 2008/0234736 A1 | 9/2008 | Trieu et al. |
| 2010/0145386 A1 | 6/2010 | Greenhalgh et al. |
| 2010/0191287 A1* | 7/2010 | Bucci ................. A61B 17/7062 606/249 |
| 2010/0234888 A1 | 9/2010 | McClintock et al. |

OTHER PUBLICATIONS

International Preliminary Report on Patentability for PCT/US2012/049959, dated Feb. 20, 2014.
European Search Report for European Application No. 12821837.7, dated Sep. 29, 2015.

* cited by examiner

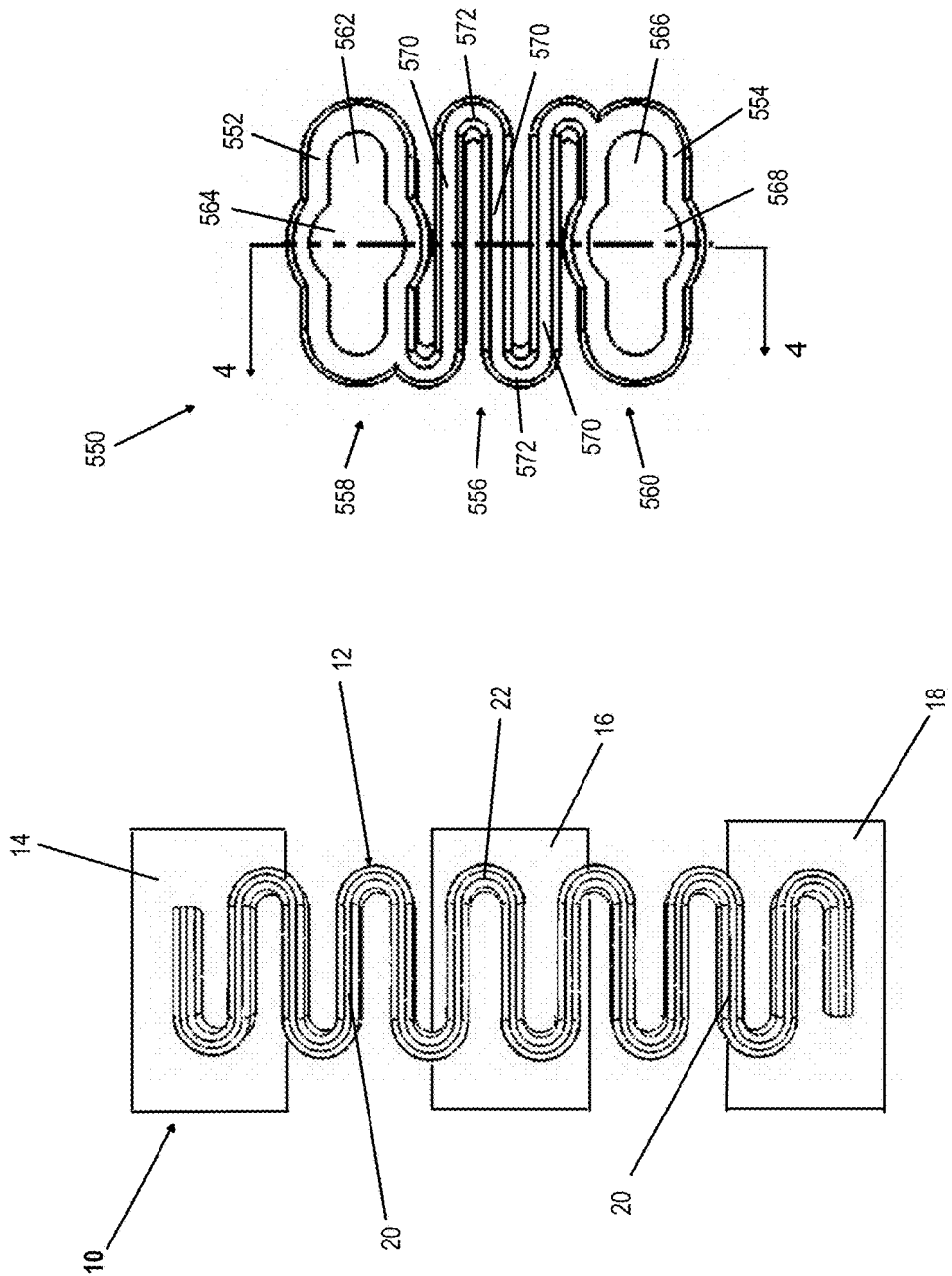

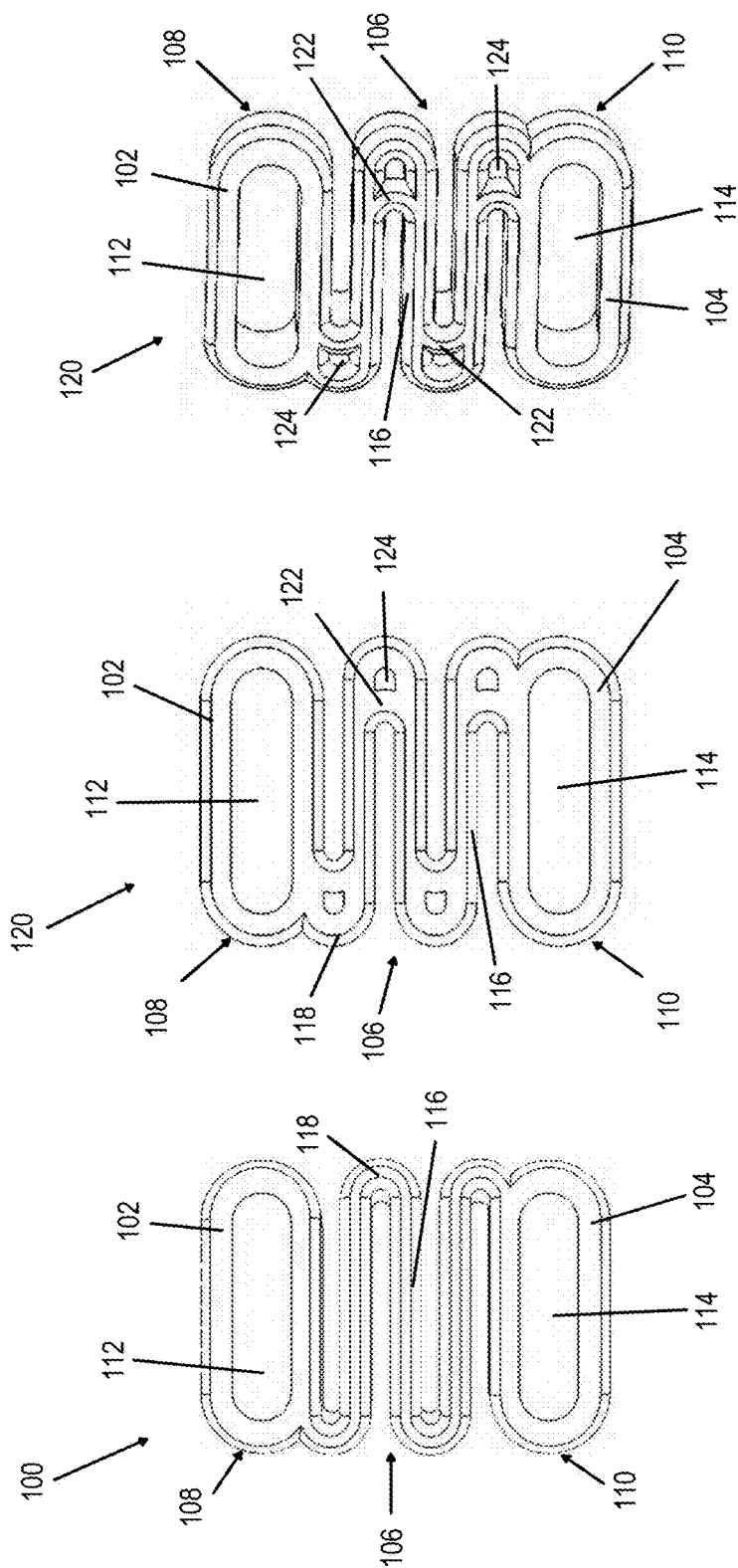

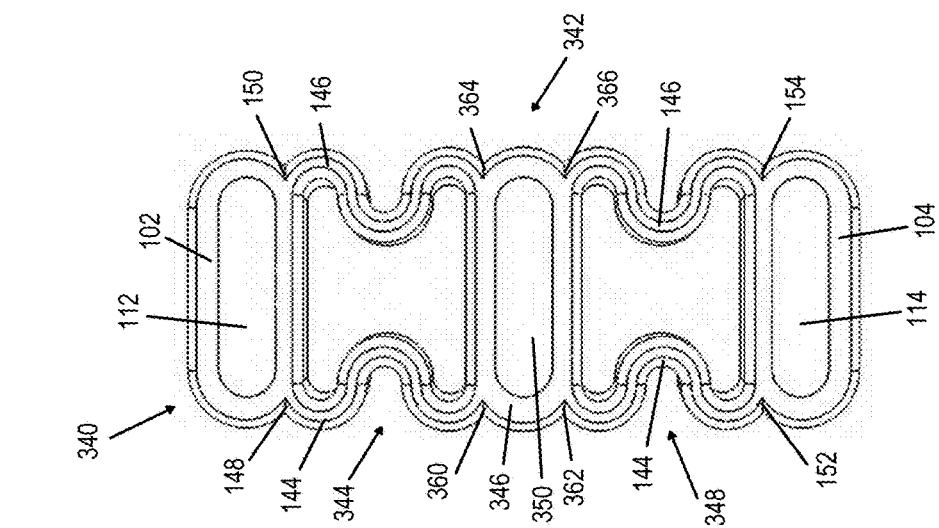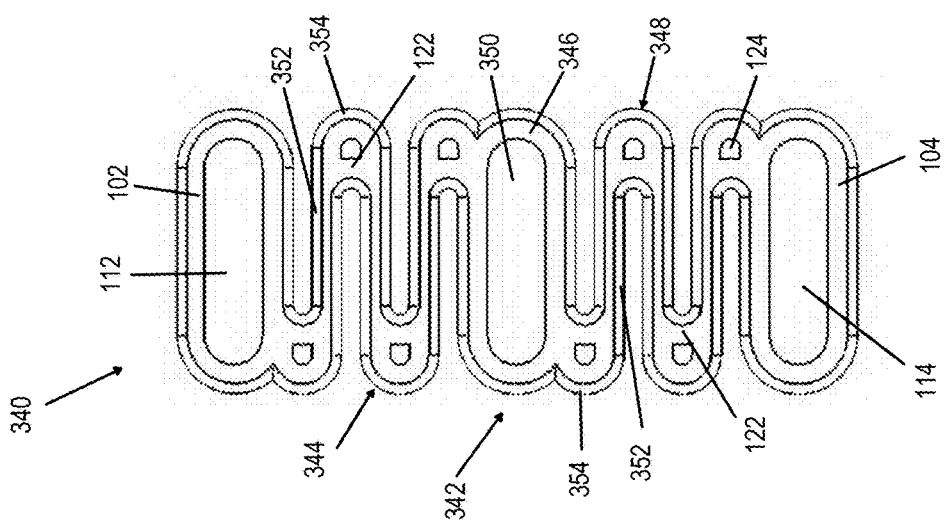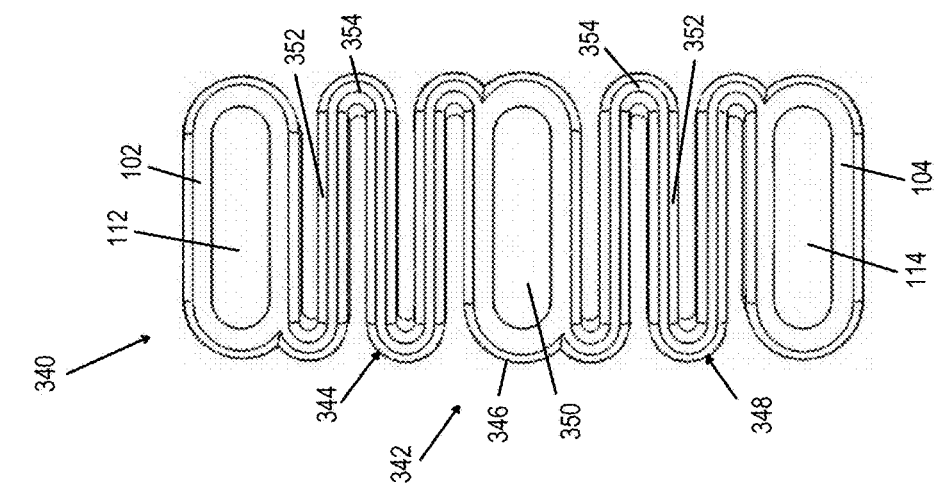

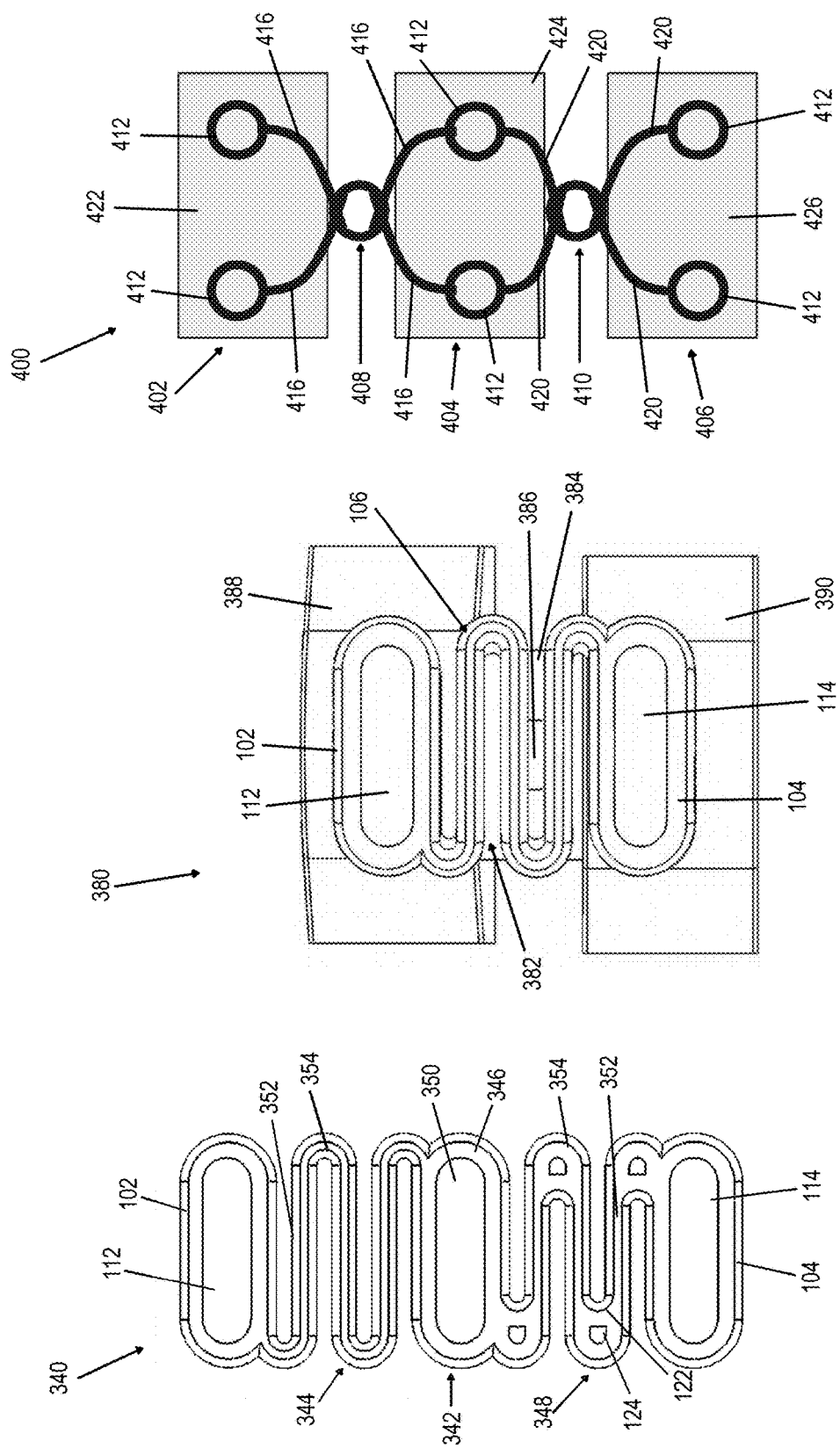

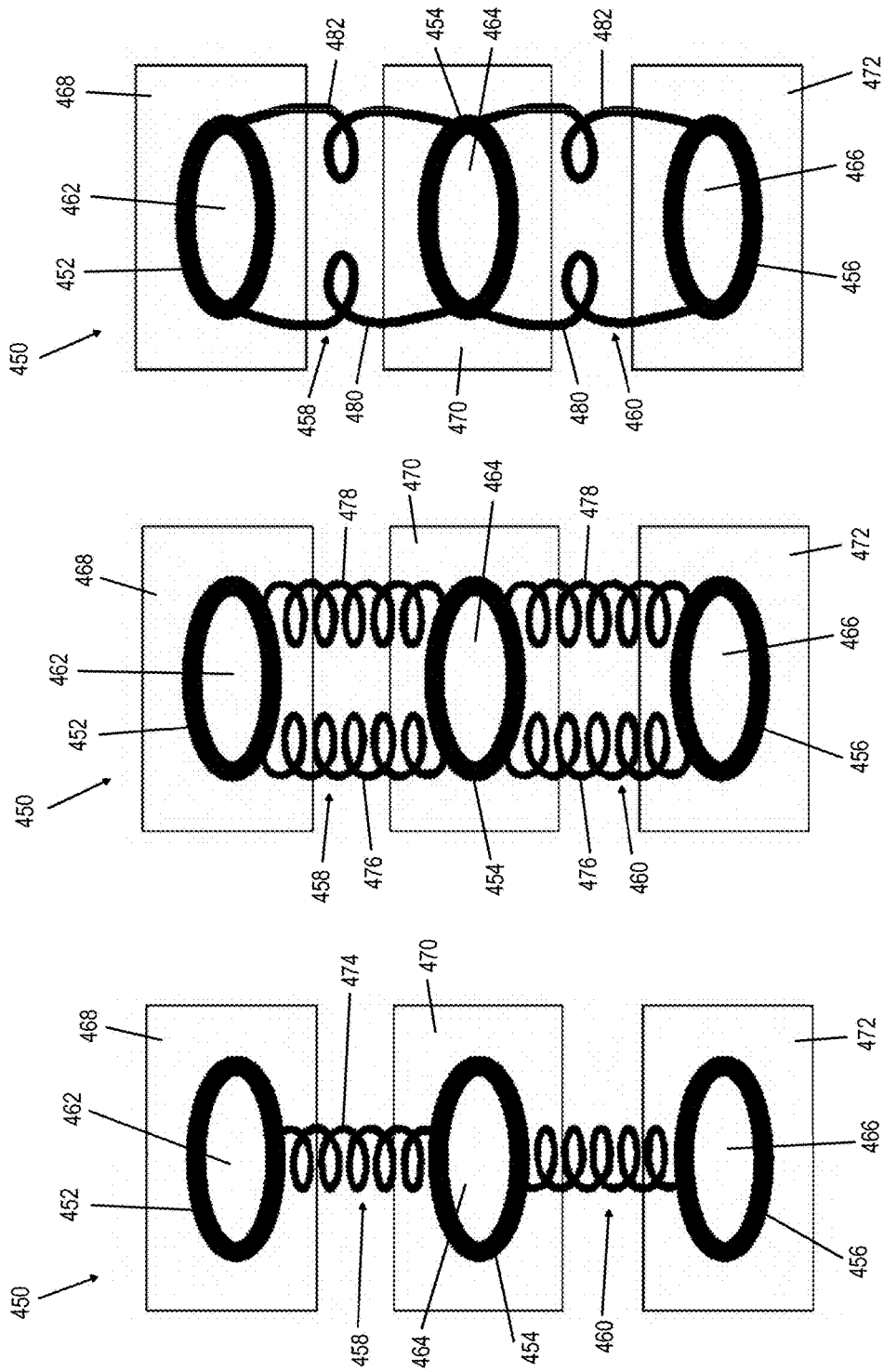

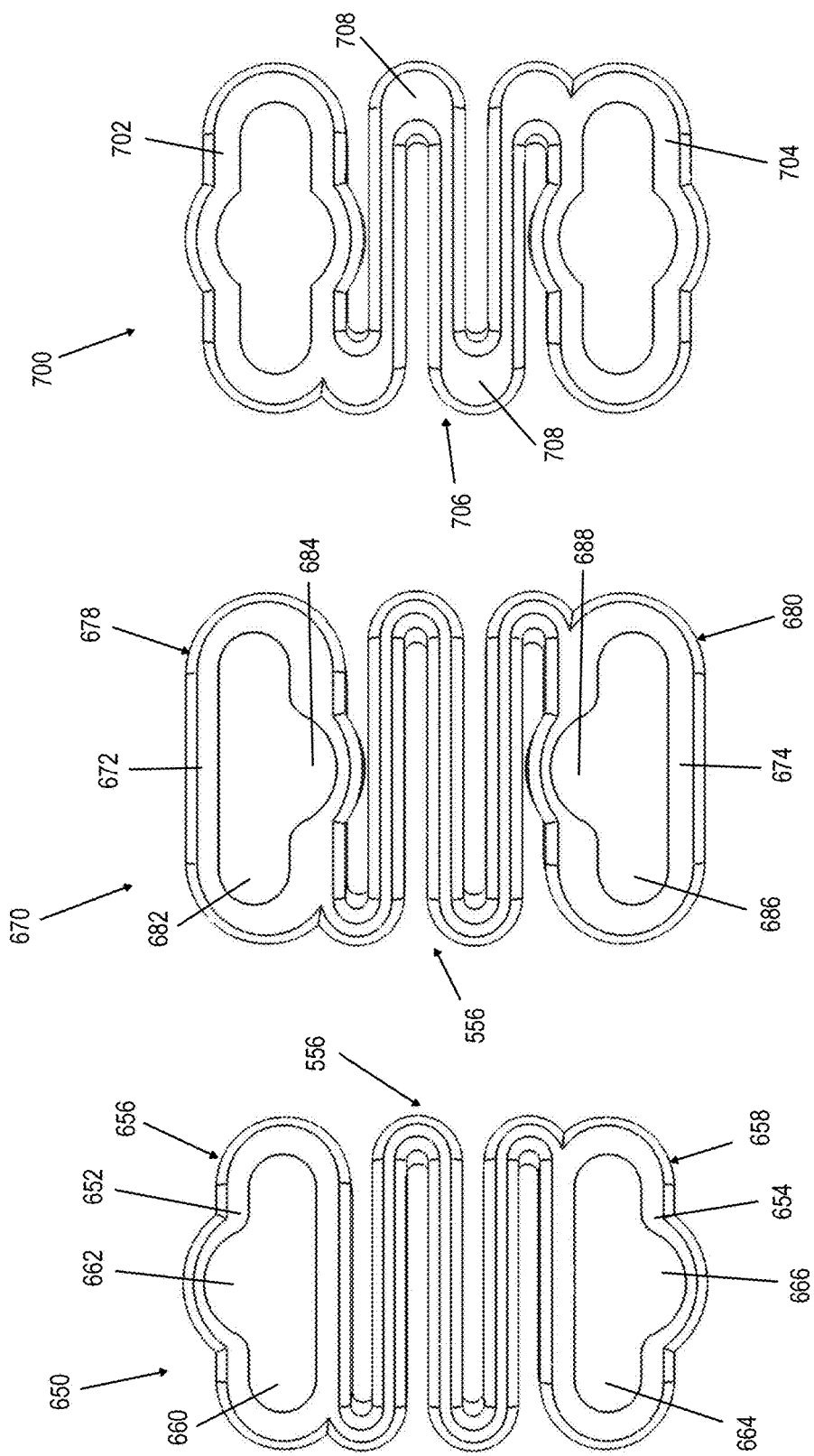

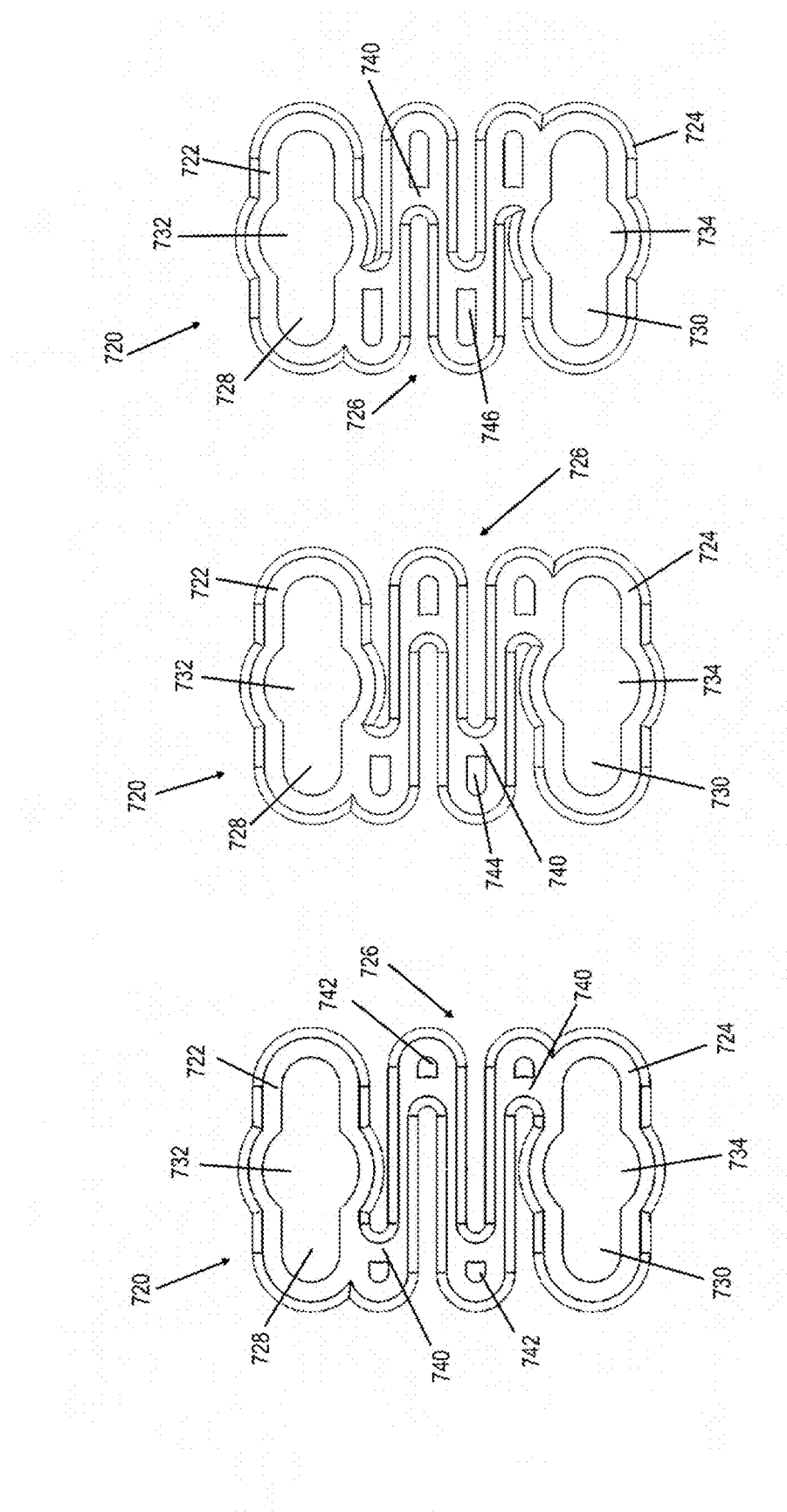

US 9,788,864 B2

DYNAMIC SPINAL FIXATION SYSTEM, METHOD OF USE, AND SPINAL FIXATION SYSTEM ATTACHMENT PORTIONS

CROSS REFERENCE TO RELATED APPLICATION

This application is a continuation of U.S. application Ser. No. 14/237,733 filed May 16, 2014, which is a national stage filing under section 371 of International Application No. PCT/US2012/049959 filed on Aug. 8, 2012 and published in English on Feb. 14, 2013 as WO 2013/022944 A1 and claims priority benefit under 35 U.S.C. §119(e) of U.S. provisional patent application Nos. 61/574,662 and 61/574,636 filed Aug. 8, 2011 and U.S. provisional patent application Nos. 61/628,662 and 61/628,663 filed Nov. 4, 2011, which are incorporated herein by reference in their entireties.

BACKGROUND OF THE INVENTION

The present disclosure relates generally to a spinal fixation device and, in particular, to a dynamic spinal fixation system and method of use for stabilizing one or more levels of the cervical spine or lumbar spine as well as to a spinal fixation system including attachment portions with reliefs. When non-surgical treatments of spinal injuries, diseases, and trauma fail, anterior spinal surgery is often performed to access the cervical or lumbar vertebrae or intervertebral discs. The anterior spinal surgery that is performed may be an anterior cervical discectomy and fusion ("ACDF"). During an ACDF procedure a bone graft or interbody implant is often used to replace the removed disc and a spinal fixation plate is then attached to adjacent vertebrae to stabilize the spine and foster arthrodesis. Current procedures employ placement of the plate first and the screws to fix that plate to vertebrae second. Most commonly, spinal fixation plates are affixed to the vertebrae using bone screws.

The currently available spinal fixation plates or devices limit visualization of the vertebrae during placement. In addition, currently available spinal fixation devices are difficult to place along the midline. The currently available spinal fixation devices also create an inability to align intervening segments for fixation. Finally, the currently available spinal fixations devices make it difficult to pull the vertebrae up into a more lordotic position when significant kyphosis exists.

Accordingly, the present invention contemplates new and improved spinal fixation systems which overcome the above-referenced problems and others.

SUMMARY OF THE INVENTION

The present invention is directed toward devices and methods for use in stabilizing one or more levels of the cervical spine or lumbar spine.

In one aspect of the present invention provided herein, is a dynamic spinal fixation system. The dynamic spinal fixation system includes a member with a superior end and an inferior end. The member includes a first attachment portion with a first opening at the superior end and a second attachment portion with a second opening at the inferior end. An intermediate portion connects the first attachment portion and the second attachment portion.

In another embodiment of the present invention provided herein, is a dynamic spinal fixation system. The dynamic spinal fixation system includes a member with a top end and a bottom end. The member includes a first attachment portion with a first opening at the top end and a second attachment portion with a second opening at the bottom end. An intermediate portion connects the first attachment portion and the second attachment portion. At least one of the first and second openings includes a relief.

In a further aspect of the present invention provided herein, is a surgical method for fusing a spine. The method includes obtaining a dynamic spinal fixation system. The dynamic spinal fixation system includes a member with a superior end and an inferior end. The member includes a first attachment portion at the inferior end which includes a first opening with a first relief and a second attachment portion which includes a second opening with a second relief. An intermediate portion connects the first attachment portion and the second attachment portion. A first bone fastener is inserted into a first vertebra of a patient and a second bone fastener is inserted into a second vertebra of the patient. The first vertebra is superior the second vertebra. The first relief is then aligned with the first fastener and the second relief is aligned with the second fastener. The member is moved into alignment with the first vertebra and the second vertebra for fixation by sliding the member to engage the first fastener in the first opening and second fastener in the second opening. The first fastener is tightened to the first vertebra and the second fastener is tightened to the second vertebra to secure the dynamic spinal fixation system to at least the first vertebra and the second vertebra of a patient's spine. The method is advantageous because it provides a surgeon with the ability to place the bone fasteners into the spine prior to placement of the dynamic spinal fixation system which assists in placing the system in the midline of the spine while also allowing for ideal fastener placement with respect to the vertebrae.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 1 shows a front view of one embodiment of a two level dynamic spinal fixation system, in accordance with an aspect of the present invention;

FIG. 2 shows a front view of one embodiment of a one level dynamic spinal fixation system including reliefs, in accordance with an aspect of the present invention;

FIG. 6 is another embodiment of a one level dynamic spinal fixation system from a front view, in accordance with an aspect of the present invention;

FIG. 7 shows a front view of yet another embodiment of a one level dynamic spinal fixation system, in accordance with an aspect of the present invention;

FIG. 8 is a perspective view of the dynamic spinal fixation system embodiment of FIG. 7, in accordance with an aspect of the present invention;

FIG. 21 is a front view of a two level embodiment of the dynamic spinal fixation system of FIG. 8, in accordance with an aspect of the present invention;

FIG. 22 is a front view of a two level embodiment of the dynamic spinal fixation system of FIG. 9, in accordance with an aspect of the present invention;

FIG. 23 is a front view of a two level embodiment of the dynamic spinal fixation system of FIG. 10, in accordance with an aspect of the present invention;

FIG. 24 is a front view of a two level dynamic spinal fixation system embodiment that combines the dynamic fixation systems of FIG. 8 and FIG. 9, in accordance with an aspect of the present invention;

FIG. 25 is a front view of the one level dynamic spinal fixation system embodiment of FIG. 8 integrated with an interbody cage, in accordance with an aspect of the present invention;

FIG. 26 is a front view of another embodiment of a two level dynamic spinal fixation system, in accordance with an aspect of the present invention;

FIG. 27 is another embodiment of a two level dynamic spinal fixation system with at least one coil spring-like member shown from a front view, in accordance with an aspect of the present invention;

FIG. 28 is a front view of yet another embodiment of a two level dynamic spinal fixation system with at least two parallel coil spring-like members, in accordance with an aspect of the present invention;

FIG. 29 is a further embodiment of a two level dynamic spinal fixation system with at least two parallel torsional spring members shown from a front view, in accordance with an aspect of the present invention;

FIG. 38 is a front view of another dynamic spinal fixation system embodiment with attachment portions including openings with off center reliefs, in accordance with an aspect of the present invention;

FIG. 39 is a front view of a further embodiment of a dynamic spinal fixation system with attachment portions including openings with reliefs, in accordance with an aspect of the present invention;

FIG. 40 is yet another embodiment of a dynamic spinal fixation system with attachment portions including openings with reliefs shown from a front view, in accordance with an aspect of the present invention;

FIG. 41 is a front view of an additional embodiment of a dynamic spinal fixation system with attachment portions including openings with reliefs, in accordance with an aspect of the present invention;

FIG. 42 is another embodiment of a dynamic spinal fixation system with attachment portions including openings with reliefs from a front view, in accordance with an aspect of the present invention;

FIG. 43 is a front view of still a further embodiment of a dynamic spinal fixation system with attachment portions including openings with reliefs, in accordance with an aspect of the present invention;

DETAILED DESCRIPTION FOR CARRYING OUT THE INVENTION

Figure 3:
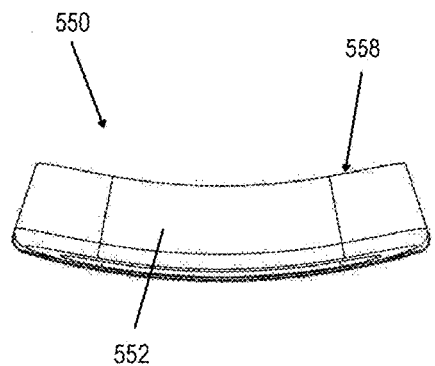
FIG. 3 shows a top view of the dynamic spinal fixation system of FIG. 2, in accordance with an aspect of the present invention.

In this application, the words proximal, distal, anterior, posterior, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body.

Referring to the drawings, wherein like reference numerals are used to indicate like or analogous components throughout the several views and referring now to FIG. 1 which depicts a dynamic spinal fixation plate or system 10. The dynamic spinal fixation system 10 includes a single member 12. The single member 12 is aligned with a first vertebra 14 at a superior end, a second vertebra 16 at a mid-point, and a third vertebra 18 at an inferior end. The system 10 may be secured to the vertebrae 14, 16, 18 using bone fasteners, not shown.

The single member 12 may be comprised of a single elastic component with a plurality of straight and curved portions. The single member 12 may be a wire, rod, tube, or other curvilinear spring-like element and may be made of a metallic, polymer, ceramic, or composite material. The single member 12 or elastic component may include a plurality of straight portions 20 and a plurality of curved portions 22 to facilitate fixation of a bone fastener, such as a screw, nail, staple, wire, pin, and the like, to the vertebrae 14, 16, 18. The plurality of straight portions 20 may preferably range from one to fifteen per level and the plurality of curved portions 22 may preferably range from one to sixteen per level. More preferably the plurality of straight portions 20 may range from one to six per level and the plurality of curved portions 22 may range from one to seven per level. In the depicted embodiment, the single member 12 includes thirteen straight portions 20 and twelve curved portions 22. The bone fasteners may be placed through the single member 12 to engage the vertebrae, specifically the bone fasteners may be placed through any two horizontal sections of the single member 12. In alternative embodiments, the single member 12 may include attachment portions at the positions where the single member 12 is secured to the vertebrae and the attachment portions may have closed geometries of the types described in greater detail below.

In addition, the shape of the single member 12 may also facilitate controlled deformation in axial compression and in flexion/extension while maintaining a high level of rigidity in lateral bending and in the anterior/posterior direction. The single member 12 of the dynamic spinal fixation system 10 may be comprised of at least one spring-like elastically deformable element. The spring-like element may be curvilinear in shape and allow for elastic deformation when loaded. The deformation of the spring-like element is primarily in the axial direction allowing for controlled or limited flexion and extension. Further, the single member 12 may be shaped to match the curvature of the spine in the sagittal and transverse planes. Alternative shapes that are advantageous to promote stability or arthrodesis of the spine are also contemplated.

The single member 12 may have a cross-section that is circular, elliptical, square, rectangular, or another uniform or non-uniform geometric shape. In addition, the single member 12 may have a uniform geometry along the sagittal and/or transverse planes. Alternatively, the single member 12 may have a non-uniform geometry along the sagittal and/or transverse planes, whereby the single member 12 changes in thickness becoming either thicker or thinner along the sagittal and/or transverse planes. For example, the single member 12 may be thicker near the lateral aspects of the dynamic spinal fixation system 10 and may be thinner near the midline of the dynamic spinal fixation system 10. A system 10 with thicker lateral aspects and thinner near the midline gives the single member 12 a larger cross-section dimension at the lateral sides of the system 10 and a smaller cross-section dimension near the midline of the system 10. The single member 12 may also be reinforced with an absorbable biomaterial that is resorbed over time and as the biomaterial is absorbed, the stiffness of the dynamic spinal fixation systems changes.

The system 10 provides for a high proportion of open area between plurality of straight and curved portions of the single member 12 allowing for easy visualization through the single member 12. The system 10 also provides elastic compliance allowing the single member 12 to be pre-compressed or pre-distracted prior to attachment to the vertebrae 14, 16, 18. By pre-compressing the single member 12, the system 10 can facilitate pre-distraction of one or more motion segments of the spine when attached to the vertebrae 14, 16, 18. Alternatively, by pre-distracting the single member 12, the system 10 can facilitate pre-compression of one or more motion segments of the spine when attached to the vertebrae 14, 16, 18.

Referring now to FIGS. 2-5, an alternative embodiment of a dynamic spinal fixation system or plate 550 is shown. The system 550 includes a superior end 558 and an inferior end 560. A first attachment portion 552 is at the superior end 558 of the system 550 and a second attachment portion 554 is at the inferior end 560 of the system 550. An intermediate portion 556 connects the first attachment portion 552 and the second attachment portion 554. The first attachment portion 552 and second attachment portion 554 or platform sections may have a generally closed geometry such as a circle, ellipse, square, rectangle, or other closed geometry to facilitate placement of bone fasteners, such as bone screws, nails, staples, wires, pins, and the like. The first attachment portion 552 includes a first opening or slot 562 which is oriented in a transverse direction and further includes a relief 564 or a larger aperture creating a "key hole" slot. Likewise, second attachment portion 554 includes a second opening or slot 566 which is oriented in a transverse direction and further includes a relief 568 or larger aperture creating a "key hole" slot. The reliefs 564, 568 are centered in the first and second openings 562, 566, respectively. In alternative embodiments, the openings 562, 566 could also include additional reliefs allowing for additional bone fasteners to be inserted into the vertebrae before placement of the system 550 onto a patient's spine. In other alternative embodiments, the openings 562, 566 could also be oriented vertically or in any other direction. Multiple openings or tracks 562, 566 in each attachment portion 552, 554 may also be included in alternative embodiments.

Figure 4:
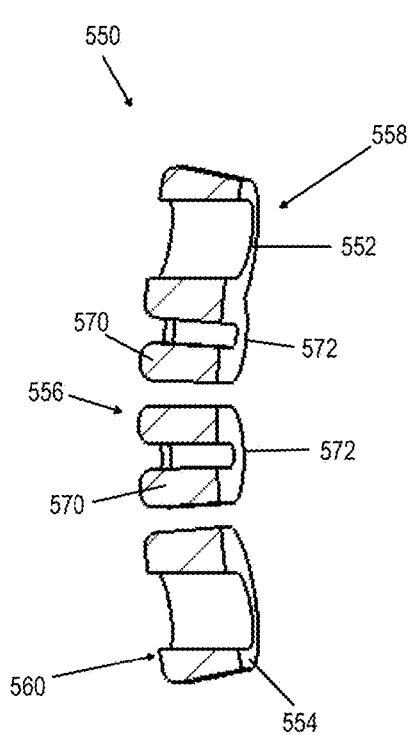
FIG. 4 is a cross-sectional perspective view of the dynamic spinal fixation system shown in FIG. 2 as viewed along section line 4-4 in FIG. 2, in accordance with an aspect of the present invention.
Figure 5:
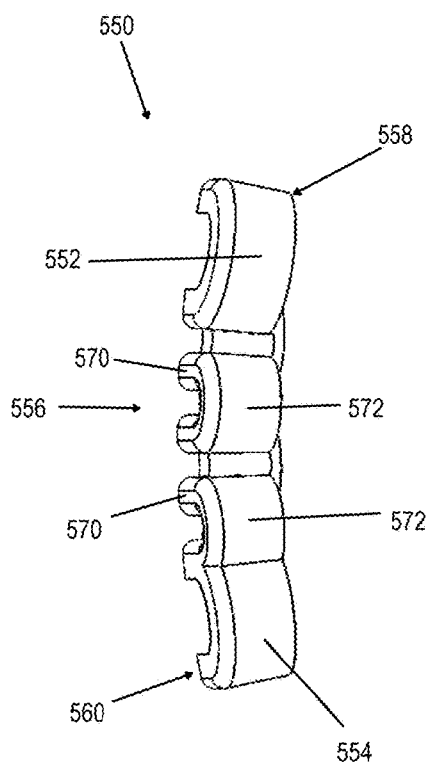
FIG. 5 is a side perspective view of the dynamic spinal fixation system shown in FIG. 4, in accordance with an aspect of the present invention.

The reliefs 564, 568 allow the first attachment portion 552 and second attachment portion 554 to be placed over the bone fastener heads, such as screw heads, that are already fixed to a vertebral body. The bone fasteners could also be pins, wires, nails, or any other method for fixing system 550 to a bone. The first and second openings 562, 566 are smaller than the geometry of the head of the bone fastener and the reliefs 564, 568. Thus, the geometry of the first and second openings 562, 566, respectively, allows the first and second attachment portions 552, 554 to be captured between the bone fastener heads and the underlying vertebra when the system 550 is slid into position between the head of the bone fasteners and the vertebra. Once the system 550 is in a desired position the surgeon may insert additional bone fasteners to secure the system 550 to the patient's spine The intermediate portion 556 may be comprised of an elastic mechanism that includes a plurality of straight portions 570 and a plurality of curved portions 572. The straight portions 570 and the curved portions 572 of the elastic mechanism provide open areas to allow for easy spine visualization through the system 550. The elastic mechanism of the intermediate portion 556 may be curvilinear in shape and allow for elastic deformation in any direction when loaded. The deformation of the elastic mechanism or spring-like element is primarily in the axial direction allowing for flexion and extension. The system 550 is designed to be flexible in the superior/inferior direction and more rigid in lateral bending and torsion. Further, the system 550 may be shaped to match the curvature of the spine in the sagittal and transverse planes. As best seen in FIG. 3, the system 550 is curved in the transverse plane to correspond to the shape of the vertebrae. A cross-sectional view of system 550 taken along line 4-4 is shown in FIG. 4 and a side view of the system 550 from FIG. 4 is shown in FIG. 5. The system 550 may also be curved in the sagittal plane to correspond to the shape of the spine. The intermediate portion 556 may be made of a non-uniform geometric shape and have a uniform or non-uniform cross-sectional geometry.

Referring now to FIG. 6, another embodiment dynamic spinal fixation system or plate 100 is shown. The system 100 includes a first attachment portion 102, a second attachment portion 104, and an intermediate portion 106 connecting the first attachment portion 102 and the second attachment portion 104. The first attachment portion or platform 102 is at a superior end 108 of the system 100 and the second attachment portion or platform 104 is at an inferior end 110. The first attachment portion 102 and second attachment portion 104 may be rigid sections for affixing the system 100 to the vertebrae. The intermediate portion 106 may be comprised of an elastic mechanism that has a less rigid elastic member with spring-like section for fostering controlled deformation.

The first attachment portion 102 includes a first opening 112 and the second attachment portion 104 includes a second opening 114. The openings 112 and 114 may be used to secure the system 100 to at least two adjacent vertebrae using bone fasteners. The uniform openings 112 and 114 allow for bone fastener placement anywhere along the openings 112 and 114. Alternatively, the first and second attachment portions 102 and 104 may include solid sections with at least one aperture through the attachment portions 102 and 104 to allow for placement of bone fasteners through the attachment portions 102 and 104 at pre-designated locations.

The intermediate portion 106 may be comprised of an elastic mechanism that includes a plurality of straight portions 116 and a plurality of curved portions 118. The straight portions 116 and the curved portions 118 of the elastic mechanism provide open areas to allow for easy spine visualization through the system 100. The elastic mechanism of the intermediate portion 106 may be curvilinear in shape and allow for elastic deformation in any direction when loaded. The deformation of the elastic mechanism or spring-like element is primarily in the axial direction allowing for flexion and extension. The system 100 is designed to be flexible in the superior/inferior direction and more rigid in lateral bending and torsion. Further, the system 100 may be shaped to match the curvature of the spine in the sagittal and transverse planes.

As seen in FIGS. 7 and 8, the dynamic spinal fixation system or plate 120 includes a first attachment portion 102, a second attachment portion 104, an intermediate portion 106, and at least one support strut 122. The first attachment portion 102 and second attachment portion 104 are of the type described above with reference to FIG. 6. The support struts 122 may be lateral to the midline to enhance the rigidity of the elastic mechanism, in particular in bending and torsion, while still allowing the system 120 to deform elastically. In alternative embodiments the support struts 122 may be along the midline of the system 120. The support struts 122 provide at least one additional support between the straight portions 116 of the intermediate portion 106 and may be generally parallel to the curved portions 118. In alternative embodiments, the struts 122 may have a radius of curvature smaller than the radius of curvature of the curved portions 118. The support struts 122 also create an opening 124 between the curved portions 118 and the support struts 122. In the depicted embodiment there are four support struts 122. Additional support struts may also be added generally in parallel with the support struts 122 to provide additional rigidity to the intermediate portion 106.

Figure 9:
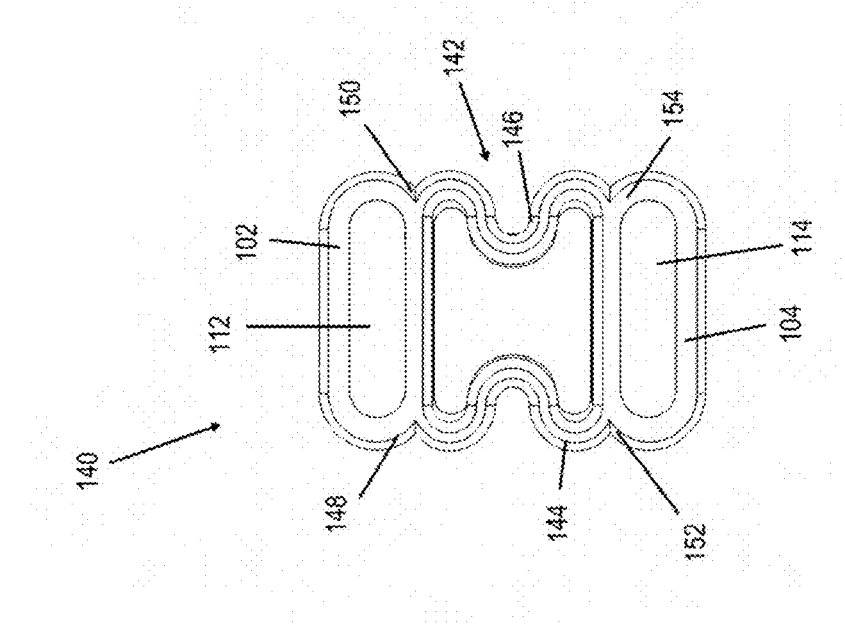
FIG. 9 is an additional embodiment of a one level dynamic spinal fixation system from a front view, in accordance with an aspect of the present invention.

Another dynamic spinal fixation system 140 or plate is shown in FIG. 9. The system 140 includes first attachment portion 102, second attachment portion 104, and intermediate portion 142. The first attachment portion 102 and second attachment portion 104 are of the type described above with reference to FIGS. 6-8. The intermediate portion 142 may include two or more separate portions. In the depicted embodiment of system 140 the intermediate portion 142 includes a first intermediate side 144 parallel to a second intermediate side 146. The first intermediate side 144 is a mirror image of the second intermediate side 146. The intermediate portion 142 connects the first attachment portion 102 and the second attachment portion 104. The first intermediate side 144 mates with the inferior side of the first attachment portion 102 on a first lateral end 148 and with the superior side of the second attachment portion 104 on a first lateral end 152. The second intermediate side 146 mates with the inferior side of the first attachment portion 102 on a second lateral end 150 and with the superior side of the second attachment portion 104 on a second lateral end 154. The intermediate portion 142 is less rigid than the first and second attachment portions 102, 104 to allow for controlled elastic deformation. The spring-like elastic first intermediate side 144 and second intermediate side 146 enhance the rigidity of the two or more sides 144, 164, in particular in bending and torsion, while still allowing the system to deform elastically.

Figure 10:
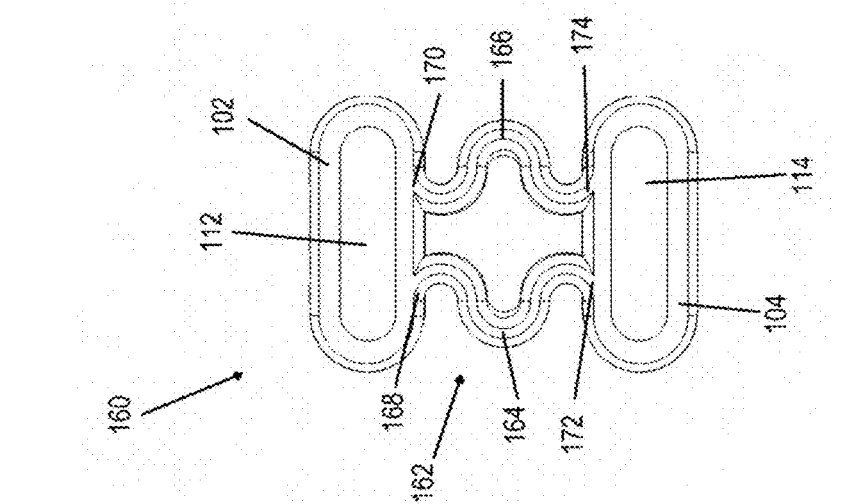
FIG. 10 shows a further embodiment of a one level dynamic spinal fixation system from a front view, in accordance with an aspect of the present invention.

Referring now to FIG. 10, a dynamic spinal fixation system 160 is shown. The dynamic spinal fixation system 160 includes first attachment portion 102, second attachment portion 104, and intermediate portion 162. The first attachment portion 102 and second attachment portion 104 are of the type described above with reference to FIG. 8. The intermediate portion 162 may include two or more separate sides. In the depicted embodiment of system 160, the intermediate portion 162 includes a first intermediate side 164 parallel to a second intermediate side 166. The first intermediate side 164 is a mirror image of the second intermediate side 166. The intermediate portion 162 connects the first attachment side 102 and the second attachment side 104. The first intermediate side 164 mates with an inferior side of the first attachment side 102 at a first medial position 168 and with the superior side of the second attachment portion 104 at a first medial position 172. The second intermediate side 166 mates with the inferior side of the first attachment portion 102 at a second medial position 170 and with the superior side of the second attachment portion 104 at a second medial position 174. The intermediate portion 162 is less rigid than the first and second attachment portions 102, 104 to allow for controlled elastic deformation. The system 160 allows for elastic motion primarily in the axial (flexion/extension) direction while the amount of motion in lateral bending and torsion is dictated by the configuration of the spring-like elements.

Figure 11:
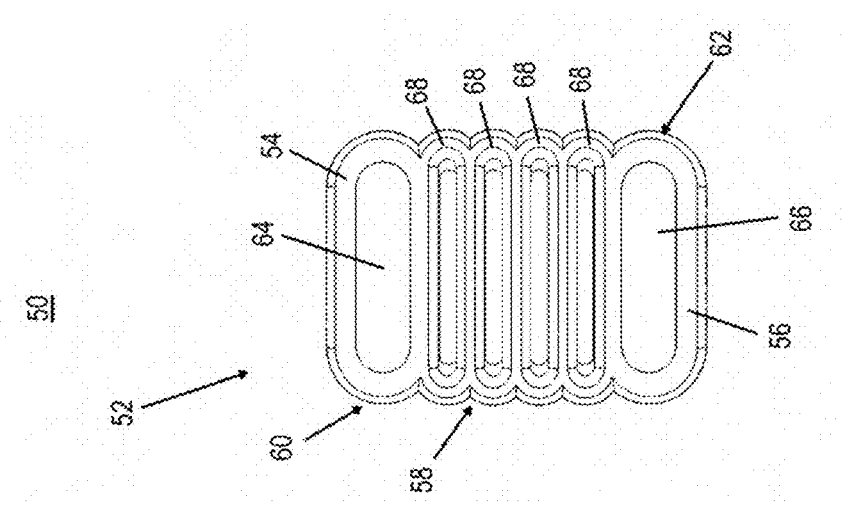
FIG. 11 shows a front view of yet another embodiment of a one level dynamic spinal fixation system, in accordance with an aspect of the present invention.

Referring now to FIG. 11, an alternative embodiment of a dynamic spinal fixation system or plate 50 is shown. The system 50 includes a member 52 with a superior end 60 and an inferior end 62. A first attachment portion 54 is at the superior end 60 of the member 52 and a second attachment portion 56 is at the inferior end 62 of the member 52. An intermediate portion 58 connects the first attachment portion 54 and the second attachment portion 56. The first attachment portion 54 and second attachment portion 56 or platform sections may have a generally closed geometry such as a circle, ellipse, square, rectangle, or other closed geometry to facilitate placement of bone fasteners, such as bone screws, nails, staples, wires, pins, and the like. The first attachment portion 54 includes a first opening 64 and the second attachment portion 56 includes a second opening 66. The openings 64 and 66 may be used to secure the system 50 to at least two adjacent vertebrae using bone fasteners. The openings 64 and 66 allow for bone fastener placement anywhere along the openings 64 and 66 because there are no pre-designated locations for the bone fasteners. Alternatively, the first and second attachment portions 54 and 56 may include solid sections with at least one aperture through the attachment portions 54 and 56 to allow for placement of bone fasteners through the attachment portions 54 and 56 at pre-designated locations. The intermediate portion 58 includes at least one closed member 68. The closed member 68 may be elastic. In the depicted embodiment there are four closed members 68. In the preferred embodiments the closed members 68 may range from one to ten. The closed elastic members 68 may have an elliptical, circular, rectangular, square, or any other closed shape. The closed elastic members 68 may also be made of a non-uniform geometric shape and have a uniform or non-uniform cross-sectional geometry. The member 52 may be curved in the transverse plane to correspond to the shape of the vertebrae. The member 52 may also be curved in the sagittal plane to correspond to the shape of the spine.

Figure 13:
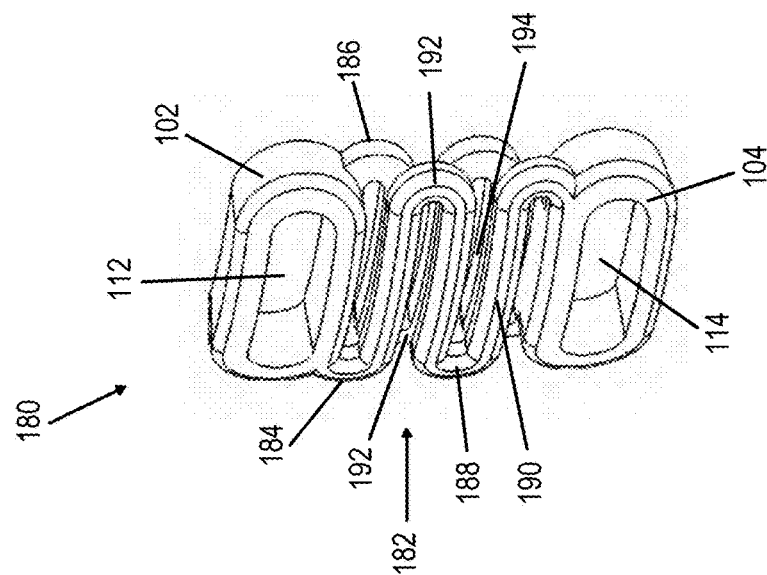
FIG. 13 is a perspective view of the dynamic spinal fixation system embodiment of FIG. 12, in accordance with an aspect of the present invention.
Figure 12:
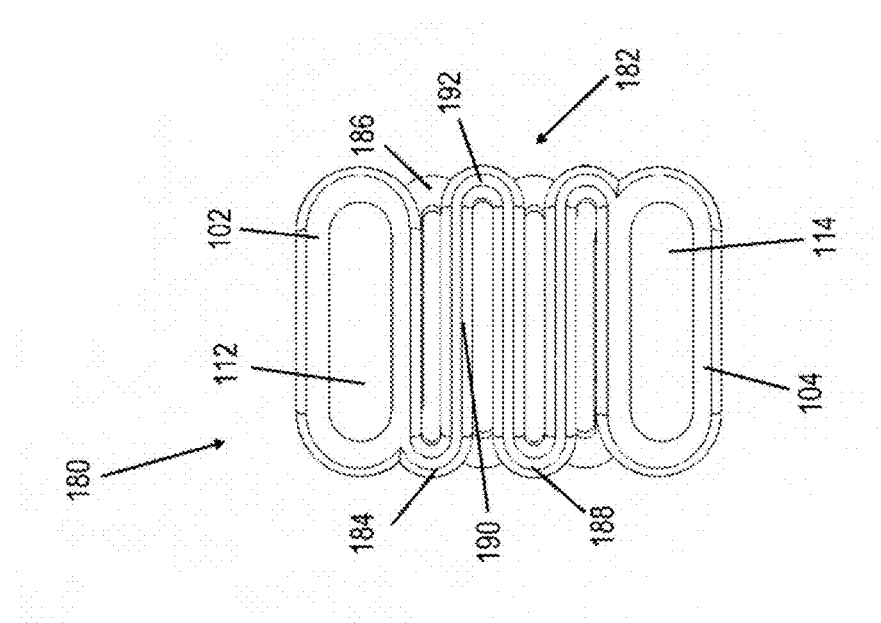
FIG. 12 is another embodiment of a one level dynamic spinal fixation system shown from a front view, in accordance with an aspect of the present invention.

Another dynamic spinal fixation system 180 is depicted in FIGS. 12 and 13. The dynamic spinal fixation system 180 includes first attachment portion 102, second attachment portion 104, and an intermediate portion 182. The intermediate portion 182 includes a first intermediate side 184 and a second intermediate side 186. The first attachment portion 102, second attachment portion 104, and the first intermediate side 184 are of the type described above with reference to FIG. 6. The second intermediate side 186 is a mirror image of the first intermediate side 184. The first intermediate side 184 includes a first plurality of curved portions 188 and a first plurality of straight portions 190. The second intermediate side 186 includes a second plurality of curved portions 192 and a second plurality of straight portions 194. The first intermediate side 184 is connected to the first attachment portion 102 and the second attachment portion 104 on the anterior aspect and the second intermediate side 186 is connected to the first attachment portion 102 and the second attachment portion 104 on the posterior aspect. The first intermediate side 184 overlaps with the second intermediate side 186. The first plurality of straight portions 190 and the second plurality of straight portions 194 are aligned while the first plurality of curved portions 188 and the second plurality of curved portions 192 are opposite each other. In alternative embodiments, the plurality of curved portions could be aligned and the plurality of straight portions could be offset. The intermediate portion 182 enhances rigidity by adding a second intermediate side 186 to the first intermediate side 184. However, even with the enhanced rigidity of the intermediate portion 182, the system 180 is able to deform elastically. Additional intermediate portions could also be added to further enhance rigidity of the system 180 while still allowing the system 180 to deform elastically. The first intermediate side 184 and the second intermediate side 186 may have uniform or non-uniform cross-sectional geometry.

Figure 14:
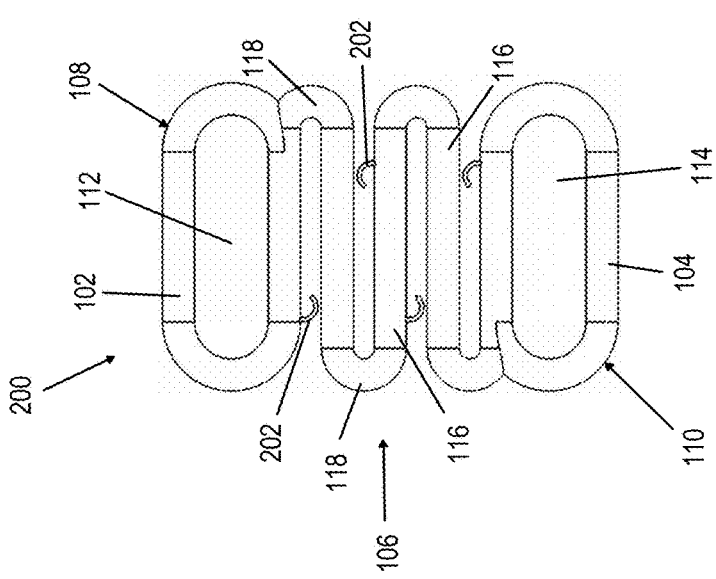
FIG. 14 shows another embodiment of a one level dynamic spinal fixation system with a hard stop from a front view, in accordance with an aspect of the present invention.

Referring now to FIG. 14, another embodiment dynamic spinal fixation system 200 is shown. The system 200 is of the type described above with reference to FIG. 6 including a first attachment portion 102, a second attachment portion 104, and an intermediate portion 106. The system 200 further includes at least one hard stop 202 attached to the intermediate portion 106. In the depicted embodiment there are four hard stops 202 and the hard stops 202 comprise arced members positioned between two adjacent straight portions 116. The hard stops 202 may also be placed between two adjacent curved portions 118. The hard stops 202 limit the amount of deformation of the intermediate portion 106 when the system 200 is in compression. When the system 200 experiences compressive loading or bending, the intermediate member 106 deforms until the hard stops 202 are engaged on the adjacent straight portions 116. When the hard stops 202 contact the straight portions 116 deformation is limited.

Figure 15:
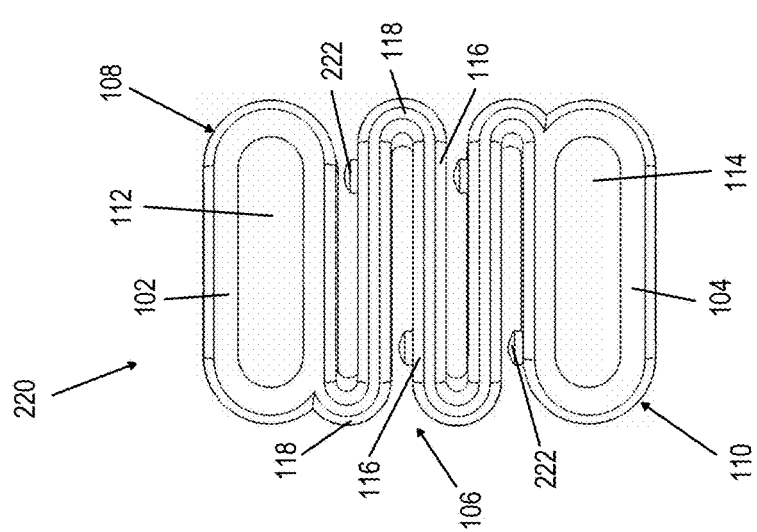
FIG. 15 is a front view of a further embodiment of a one level dynamic spinal fixation system with an alternative hard stop, in accordance with an aspect of the present invention.

Depicted in FIG. 15, is another dynamic spinal fixation system 220 including first attachment portion 102, second attachment portion 104, and intermediate portion 106 as described above with reference to FIG. 6, and further comprising at least one alternative hard stop 222. The hard stop 222 is attached to the intermediate portion 106 and has a generally domed shape. In the depicted embodiment, there are four hard stops 222 located between two adjacent straight portions 116. Although not shown, it is also contemplated that the hard stops 222 may be placed between two curved portions 118. The hard stops 222 also limit the amount of deformation in the intermediate portion 106 during compression of the system 220. During compression of the system 220, the intermediate portion 106 is squeezed together until at least one straight portion 116 makes contact with an adjacent a hard stop 222.

Figure 16:
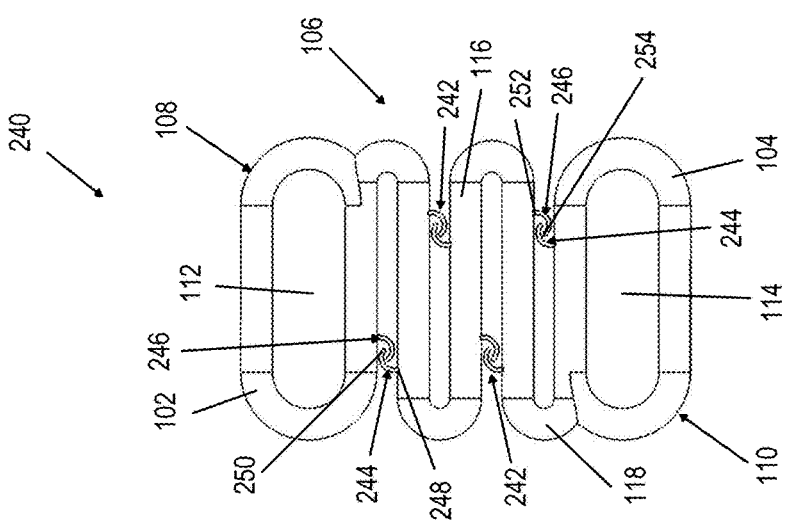
FIG. 16 is a front view of yet another embodiment of a one level dynamic spinal fixation system with a further alternative hard stop, in accordance with an aspect of the present invention.

FIG. 16 illustrates another embodiment dynamic spinal fixation system 240 including first attachment portion 102, second attachment portion 104, and intermediate portion 106 as described above with reference to FIG. 6, and further comprising at least one alternative hard stop 242. The hard stops 242 are redundant hard stops. In the depicted embodiment, there are four hard stops 242. The hard stop 242 includes a first member 244 and a second member 246. The first member 244 is arced from a first end 248 to a second end 250. The second member 246 is also arced from a first end 252 to a second end 254. The first end 248 of the first member 244 and the first end 252 of the second member 246 are attached to adjacent straight portions 116. While the second end 250 of the first member 244 and the second end 254 of the second member 246 are arced towards each other in order for second end 250 to overlap with second end 254.

Under compressive loading, tensile loading, or bending the intermediate portion 106 deforms until the hard stops 242 are engaged on the mating features, which include the first member 244, the second member 246, and the second ends 250, 254 of the first member 244 and second member 246, respectively. The amount of deformation of the intermediate portion 106 is limited in compression when the first members 244 and second members 246 of the hard stops 242 contact an adjacent straight portion 116. In addition the amount of deformation of the intermediate portion 106 is also limited in tension when the second end 250 of the first member 244 and the second end 254 of the second member 246 engage each other.

The intermediate members 58, 106, 142, 162, 182, and 556, of FIGS. 2-16 may be reinforced with an absorbable biomaterial that is resorbed over time and as the biomaterial is absorbed, the stiffness of the dynamic spinal fixation systems changes.

Figure 17:
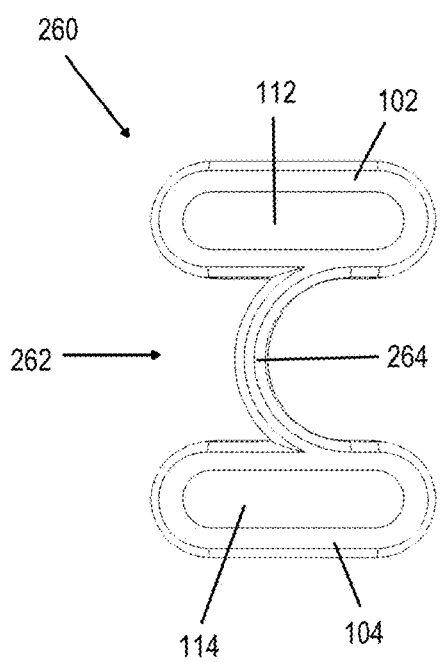
FIG. 17 shows a front view of an additional embodiment of a one level dynamic spinal fixation system, in accordance with an aspect of the present invention.

Referring now to FIG. 17, yet another embodiment dynamic spinal fixation system 260 is shown. The system 260 including first attachment portion 102 and second attachment portion 104 as described above with reference to FIG. 6, and further includes an intermediate portion 262. The intermediate portion 262 connects the first attachment portion 102 and the second attachment portion 104 and includes at least one curve 264. In the depicted embodiment the at least one curve 264 arcs in a generally medial direction relative to the system 260.

Figure 18:
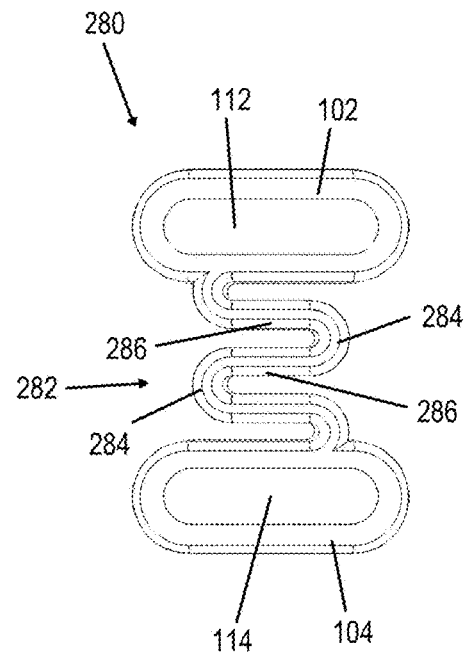
FIG. 18 shows another embodiment of a one level dynamic spinal fixation system from a front view, in accordance with an aspect of the present invention.

Another embodiment dynamic spinal fixation system 280 is illustrated in FIG. 18. The system 280 including first attachment portion 102 and second attachment portion 104 as described above with reference to FIG. 6, and further includes an intermediate portion 282. The intermediate portion 282 connects the first attachment portion 102 and the second attachment portion 104. The intermediate portion 282 is a more complex portion and includes multiple curved sections 284 and multiple straight sections 286. In the depicted embodiment the intermediate portion 282 is narrower in width than the first and second attachment portions 102, 104 and is located in a generally medial position.

Figure 19:
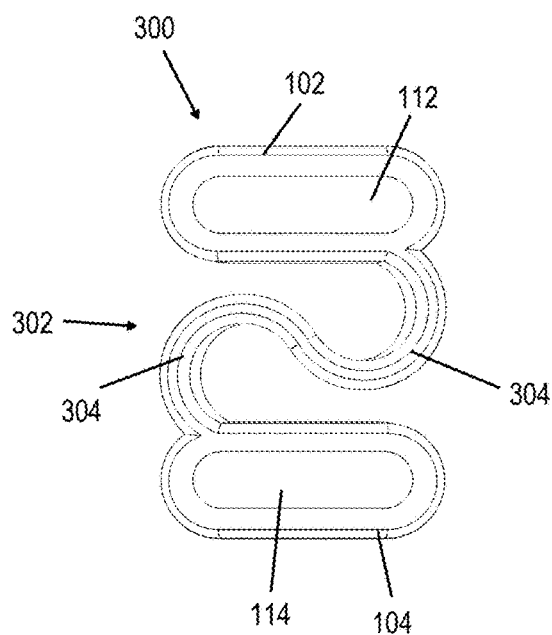
FIG. 19 shows a front view of still another embodiment of a one level dynamic spinal fixation system, in accordance with an aspect of the present invention.

Depicted in FIG. 19 is still another embodiment dynamic spinal fixation system 300. The system 300 including first attachment portion 102 and second attachment portion 104 as described above with reference to FIG. 6, and further includes an intermediate portion 302. The intermediate portion 302 connects the first attachment portion 102 and the second attachment portion 104. The intermediate portion 302 includes at least one wide curve 304 per level. In the depicted embodiment the intermediate portion 302 includes two wide curves 304.

Figure 20:
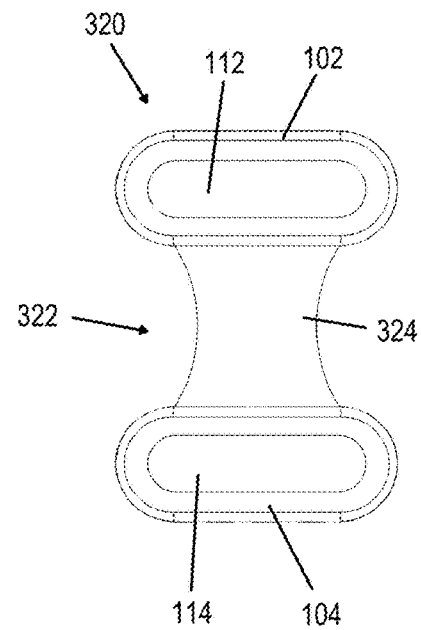
FIG. 20 shows a further embodiment of a one level dynamic spinal fixation system from a front view, in accordance with an aspect of the present invention.

Referring now to FIG. 20 another dynamic spinal fixation system 320 is shown. The system 320 includes first attachment portion 102 and second attachment portion 104 as described above with reference to FIG. 6, and further includes an intermediate portion 322. The intermediate portion 322 connects the first attachment portion 102 and the second attachment portion 104. The intermediate portion 322 includes a solid or closed elastic member or element 324. The solid member 324 may be of any shape that deforms elastically when loaded.

The intermediate portions 262, 282, 302, and 322 of FIGS. 17-20 may be made of a metal, polymer, ceramic, or composite material. Further the intermediate portions 262, 282, 302, and 322 of FIGS. 17-20, may be reinforced with an absorbable biomaterial that is resorbed over time and as the biomaterial is absorbed, the stiffness of the dynamic spinal fixation systems changes.

The dynamic spinal fixation systems of FIGS. 2-20 each illustrate a one level system. Each of the systems of FIGS. 2-20 can be modified to include additional attachment portions and either additional or elongated intermediate portions for engaging more than two adjacent vertebrae. For example and as seen in FIGS. 21-24, the dynamic spinal fixation system 340 is a two level system for the spine. The system 340 includes a first attachment portion 102 and a second attachment portion 104 as described above with reference to FIG. 8, and further includes an intermediate portion 342. The intermediate portion 342 includes a first intermediate member 344, a third attachment portion 346, and a second intermediate member 348. The first intermediate member 344 and second intermediate member 348 may be reinforced with an absorbable biomaterial that is resorbed over time and as the biomaterial is absorbed, the stiffness of the dynamic spinal fixation systems changes. The third attachment portion 346 may be rigid for affixing the system 340 to a vertebra. The third attachment portion 346 includes a third opening 350 which may be used to secure the system 340 to a vertebra using at least one bone fastener. The third opening 350 is uniform and therefore allows for placement of bone fasteners at any point along the third opening 350. The first, second, and third openings 112, 114, and 350, respectively, may include a ridge or lip for the bone fasteners to mate with when inserted into the patient's vertebrae to maintain a low profile of the first, second, and third attachment portions 102, 104, and 346, respectively. The low profile will prevent the bone fasteners from protruding above the first, second, and third attachment portions 102, 104, and 346, respectively, and agitating the patient's tissue. Alternatively, the attachment portions 102, 104, and 346 may include solid sections with at least one aperture through the platform to allow for placement of bone fasteners through the attachment portions 102, 104, and 346 at pre-designated locations.

Referring now to FIG. 21, the first intermediate member 344 and the second intermediate member 348 are of the type illustrated in FIG. 6 and described with reference to intermediate portion 106. The first intermediate member 344 and the second intermediate member 348 may each be comprised of a single elastic component including a plurality of straight portions 352 and a plurality of curved portions 354. The straight portions 352 and the curved portions 354 provide open areas that allow for easy visualization through the system 340 to a patient's spine. The first intermediate member 344 and the second intermediate member 348 may be curvilinear in shape and allow for elastic deformation in any direction when loaded. Further, the system 340 may be shaped to match the curvature of the spine in the sagittal and transverse planes.

Referring now to FIG. 22, the dynamic spinal fixation system 340 includes an alternative first intermediate member 344 and second intermediate member 348 of the types illustrated in FIG. 7 and described above with reference to intermediate portion 106 including at least one support strut 122. The first intermediate member 344 and the second intermediate member 348 may each be comprised of a single elastic component including a plurality of straight portions 352 and a plurality of curved portions 354. The support struts 122 may be lateral to the midline of the system 340 enhance the rigidity of the first intermediate member 344 and the second intermediate member 348, in particular in bending and torsion, while still allowing elastic deformation. The support struts 122 provide at least one additional rod between the straight portions 352 of the first intermediate member 344 and the second intermediate member 348 and are generally parallel to the curved portions 354. Alternatively, the struts 122 may have a radius of curvature smaller than the radius of curvature of the curved portions 118. The support struts 122 also create an opening 124 between the curved portions 354 and the support struts 122. In the depicted embodiment there are four support struts 122 for each of the first intermediate member 344 and the second intermediate member 348.

Referring now to FIG. 23, the dynamic spinal fixation system 340 includes yet another alternative first intermediate member 344 and the second intermediate member 348. The first intermediate member 344 and second intermediate member 348 are of the type illustrated in FIG. 9 and described with reference to intermediate portion 142. The first intermediate member 344 and second intermediate member 348 each include a first portion 144 parallel to a second portion 146. The first portion 144 is a mirror image of the second portion 146. The first intermediate member 344 connects the first attachment portion 102 and the third attachment portion 346. The first portion 144 mates with the inferior side of the first attachment portion 102 on a first lateral end 148 and with the superior side of the third attachment portion 346 on a first lateral end 360. The second portion 146 mates with the inferior side of the first attachment portion 102 on a second lateral end 150 and with the superior side of the third attachment portion 346 on a second lateral end 362. The second intermediate member 348 connects the third attachment portion 346 and the second attachment portion 104. The first portion 144 mates with the inferior side of the third attachment portion 346 on a first lateral end 364 and with the superior side of the second attachment portion 104 on a first lateral end 152. The second portion 146 mates with the inferior side of the third attachment portion 346 on a second lateral end 366 and with the superior side of the second attachment portion 104 on a second lateral end 154.

The intermediate portions 344 and 348 are less rigid than the first, second, and third attachment portions 102, 104, 346, respectively, to allow for controlled elastic deformation. The spring-like elastic first portions 144 and second portions 146 enhance the rigidity of the two or more intermediate portions 344 and 348, in particular in bending and torsion, while still allowing the intermediate portion to deform elastically.

Referring now to FIG. 24, the dynamic spinal fixation system 340 includes a first intermediate member 344 that is different than the second intermediate member 348. In the depicted embodiment the first intermediate member 344 is of the type illustrated in FIG. 6 and described with reference to intermediate portion 106 and the second intermediate member 348 is of the type illustrated in FIG. 7 and described with reference to intermediate portion 106 and including at least one support strut 122. The hybrid two level construct of intermediate portion 342 includes a first intermediate member 344 that is a more elastic member and a second intermediate member 348 that is a more rigid member. Alternative multi-level dynamic spinal fixation systems may include various combinations of the intermediate portions of FIGS. 2-20. Each of the intermediate portions of FIGS. 2-20 may have different medial and lateral stiffness. For example, the medial stiffness may be higher than the lateral stiffness alternatively the medial stiffness may be lower than the lateral stiffness. These hybrid multi-level systems may be used to augment the stiffness of spinal levels adjacent to a single (central) level anterior cervical discectomy and fusion ("ACDF").

Although only single and double level dynamic spinal fixation systems have been shown and described, additional levels may be added to the systems as needed to stabilize a patient spine, creating systems with three levels or more. In addition, the multi-level systems may include more than three alternating attachment portions and intermediate portions for longer ACDFs.

Illustrated in FIG. 25 is another embodiment dynamic spinal fixation system 380 of the type described above with reference to FIG. 6 and further including an interbody fusion cage device 382. The system 380 includes a first attachment portion 102, a second attachment portion 104, and an intermediate portion 106 of the type described above with reference to FIG. 6. The device 382 includes a hollow member 384 with a cavity 386. A bone graft may be inserted into the cavity 386 to allow for fusion to occur between two adjacent vertebrae. The interbody fusion cage device 382 is integrated into the dynamic spinal fixation system 380. The device 382 and system 380 may be pre-assembled prior to surgery or may be assembled during surgery. During surgery, the device 382 is placed into the disc space of the spine. Then the system 380 is aligned with a first vertebra 388 and a second vertebra 390 and may be affixed to the vertebrae using bone fasteners as described above with reference to FIG. 6. The dynamic spinal fixation systems of FIGS. 2-25 may be comprised of a metallic material, or alternatively of an elastic, hyperelastic, or deformable polymer, ceramic, or composite material.

An alternative dynamic spinal fixation system 400 is depicted in FIG. 26. The system 400 includes a first attachment portion 402, a second attachment portion 404, a third attachment portion 406, a first intermediate portion 408, and a second intermediate portion 410. The first intermediate portion 408 connects the first attachment portion 402 and the second attachment portion 404. The second intermediate portion 410 connects the second attachment portion 404 and the third attachment portion 406. The first attachment portion 402, second attachment portion 404, and third attachment portion 406 each include two bone fastener openings 412 for using to secure the system 400 to a patient's vertebrae. The first intermediate portion 408 includes a first elastic element 414, which may be a continuous curved torsional spring-like element, and four arms 416 connecting the first elastic element 414 and the fastener openings 412 of the first and second attachment portions 402 and 404, respectively. The second intermediate portion 410 includes a second elastic element 418, which may also be a continuous curved torsional spring-like element, and four arms 420 connecting the second elastic element 418 and the fastener openings 412 of the second and third attachment portions 404 and 406, respectively. The first intermediate portion 408 and second intermediate portion 410 may be reinforced with an absorbable biomaterial that is resorbed over time and as the biomaterial is absorbed, the stiffness of the dynamic spinal fixation systems changes.

The system 400 may be attached to a patient's spine by securing fastener openings 412 of the first attachment portion 402 to a first vertebra 422, fastener openings 412 of the second attachment portion 404 to a second vertebra 424, and fastener openings 412 of the third attachment portion 406 to a third vertebra 426. When loaded the system 400 deforms elastically by rotation around the torsion spring elements or the first intermediate portion 408 and second intermediate portion 410. The system 400 can be pre-compressed or pre-extended prior to attachment to a patient's first, second, and third vertebrae 422, 424, and 426, respectively, to facilitate distraction or compression, respectively.

Referring now to FIGS. 27-31, another embodiment dynamic spinal fixation system 450 is illustrated. The system 450 includes a first attachment portion 452, a second attachment portion 454, a third attachment portion 456, a first intermediate portion 458, and a second intermediate portion 460. The first attachment portion 452, second attachment portion 454, and third attachment portion 456 are more rigid for affixing the system 450 to a patient's vertebrae. The first attachment portion 452, second attachment portion 454, and third attachment portion 456 include a first opening 462, a second opening 464, and a third opening 466, respectively. The first opening 462 may be used to secure the system 100 to a first vertebra 468 using bone fasteners. The second opening 464 may be used to secure the system 100 to a first vertebra 470 using bone fasteners. The third opening 466 may be used to secure the system 100 to a first vertebra 472 using bone fasteners.

The first intermediate portion 458 and a second intermediate portion 460, or spring-like elastic sections, are less rigid than the attachment portions 452, 454, 456 for fostering controlled elastic deformation. The first intermediate portion 458 connects the first attachment portion 452 and second attachment portion 454. The second intermediate portion 460 connects the second attachment portion 454 and third attachment portion 456. As best seen in FIG. 27, the first intermediate portion 458 and second intermediate portion 460 may each include a single elastic element 474 with a plurality of coils. Alternatively and as depicted in FIG. 28, the first intermediate portion 458 and second intermediate portion 460 may each include a first elastic element 476 with a plurality of coils and a second elastic element 478 with a plurality of coils. The first elastic element 476 is parallel with the second elastic element 478 and both are comprised of elastic, metallic, spring-like components with uniform or non-uniform cross-sectional geometry. Additional parallel elastic elements could also be added to the intermediate portions 458, 460. The system 450 illustrated in FIG. 28 may also be monolithic and comprised of only a single component.

FIG. 29 depicts another embodiment of first intermediate portion 458 and second intermediate portion 460, wherein the first and second intermediate portions 458 and 460 respectively, each include a first elastic element 480 with a single coil and a second elastic element 482 with a single coil. The first elastic element 480 is parallel to the second elastic element 482. The first element 480 and second element 482 may be elastic torsional spring-like elements. Additional parallel elastic elements may be added in parallel to first and second elastic elements 480, 482.

Figure 30:
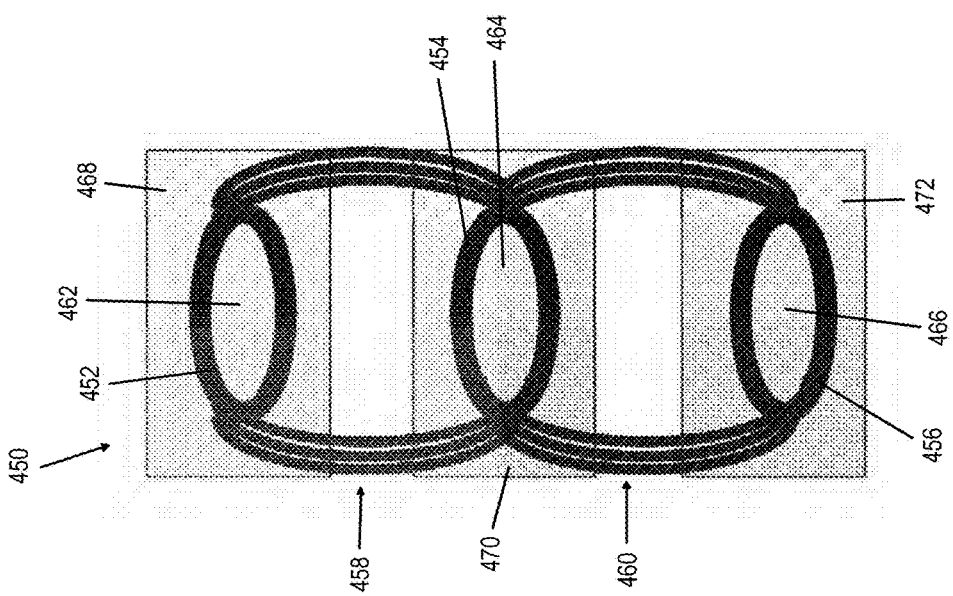
FIG. 30 is a front view of another embodiment of a two level dynamic spinal fixation system with at least two elastic members, in accordance with an aspect of the present invention.

Illustrated in FIG. 30 is another embodiment of first intermediate portion 458 and second intermediate portion 460. The first intermediate portion 458 includes a first elastic element 484 parallel to a second elastic element 486. The first element 484 and second element 486 are elastic leaf spring-like elements.

Figure 31:
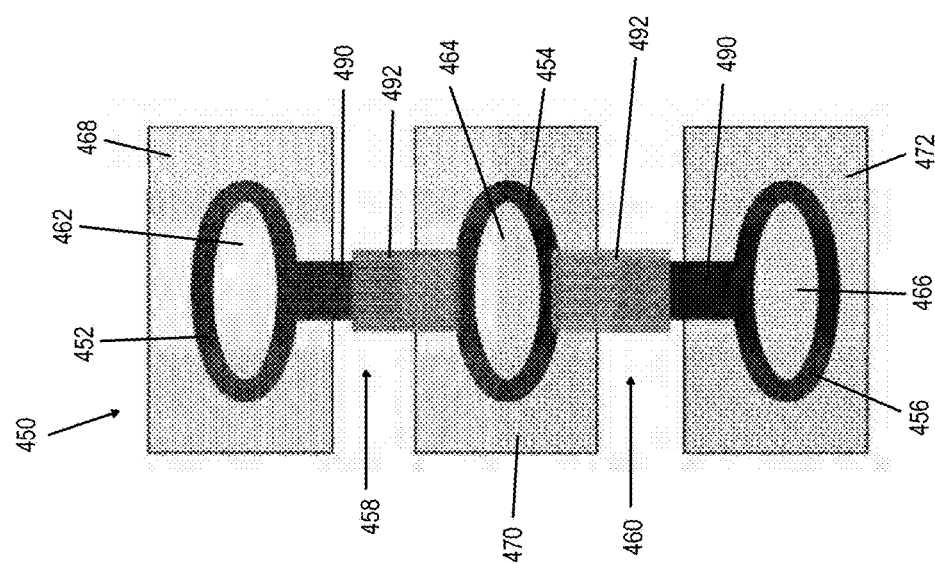
FIG. 31 is a further embodiment of a two level dynamic spinal fixation system with piston members shown from a front view, in accordance with an aspect of the present invention.

Referring now to FIG. 31, yet another embodiment of first intermediate portion 458 and second intermediate portion 460 is shown. The first intermediate portion 458 and second intermediate portion 460 include at least one piston element 490 in series with an elastic element 492. The elastic element 492 being in series with the piston element 490 offers resistance to deformation. When the system 450 deforms under a load it is guided by the piston element 490 which is rigid in all directions other than vertical. The system 450 may also be compressed or extended prior to being secured to a patient's spine to allow for pre-distraction or pre-loading of the patient's spine.

The system 450 in FIGS. 27-31 can be pre-compressed or pre-extended prior to attachment to a patient's first, second, and third vertebrae 468, 470, and 472, respectively, to facilitate distraction or compression, respectively. In addition, each configuration of the intermediate portions of system 450 allows for elastic motion primarily in the axial (flexion/extension) direction while the amount of motion in lateral bending and torsion is dictated by the configuration of the intermediate portions of the systems 450. Further, additional elastic elements may be added in parallel to the intermediate portions of the systems 450 in FIGS. 28-30 to enhance the rigidity of the system 450, in particular in bending and torsion, while still allowing the system 450 to deform elastically. The intermediate portions 458, 460 of FIGS. 27-31 can have different geometries including but not limited to simple and slightly curved or complex and multiply curved, with narrow curves or wide curves, with one, two or more curves per level. The intermediate portions 458, 460 can also be solid or closed geometries that are elastically deformable such as metals, polymers, or composites. The first intermediate portion 458 and second intermediate portion 460 of FIGS. 27-31 may be reinforced with an absorbable biomaterial that is resorbed over time and as the biomaterial is absorbed, the stiffness of the dynamic spinal fixation systems changes.

In addition, as each of the dynamic spinal fixation systems of FIGS. 26-31 have been described with reference to three sections for engaging three adjacent vertebrae and two intermediate deformable portions or compliant sections for a two-level anterior cervical discectomy and fusion ("ACDF"), it should be understood that each of the systems in FIGS. 26-31 can be modified for a single-level ACDF. A single-level ACDF would only include two sections for engaging two adjacent vertebrae and one intermediate portion or elastic section. Similarly, it should also be understood that each of the systems in FIGS. 26-31 can be modified to include more than three alternating attachment sections and intermediate sections for longer ACDF's, which may be more than two-levels.

FIGS. 32-36 show spinal fixation systems that allow the bone fasteners, for example, screws, to be secured to the vertebrae before the systems are placed onto the spine. The systems generally contain at least two attachment portions or rigid platform-like sections which are used to secure the systems to a patient's vertebrae. The attachment portions are generally more rigid than the rest of the system to facilitate bone fastener fixation to the bony vertebral bodies by allowing bone fasteners, such as screws, nails, staples, wires, pins, and the like, to pass through the systems at the attachment portion or portions.

Figure 33:
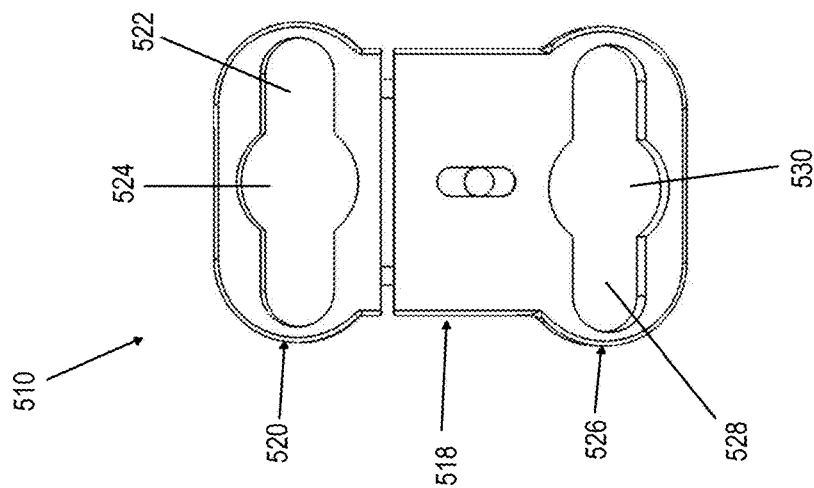
FIG. 33 is a front view of another embodiment of a dynamic spinal fixation system with attachment portions including openings with reliefs; in accordance with an aspect of the present invention.
Figure 32:
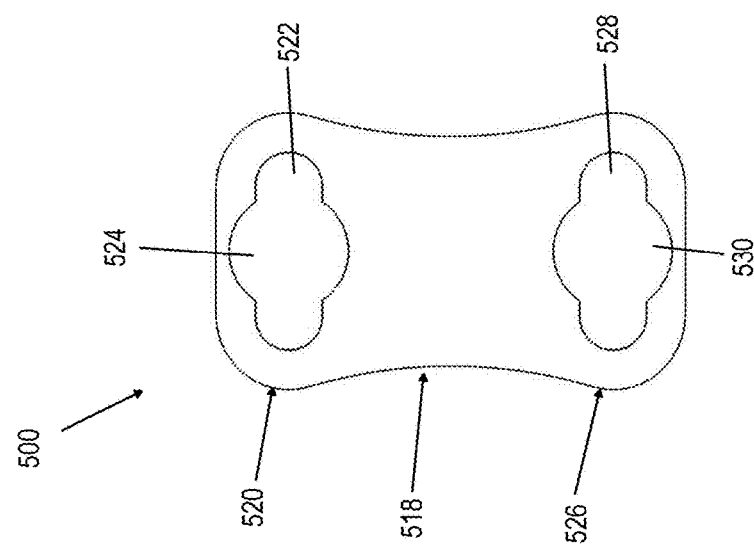
FIG. 32 is a front view of a static spinal fixation system embodiment with attachment portions including openings with reliefs, in accordance with an aspect of the present invention.

FIGS. 32 and 33 illustrate a monolithic implant 500 and a multi-component implant 510, respectively. The implant 500 is a static spinal fixation implant and the implant 510 is a dynamic implant. The implants 500, 510 each include a first attachment portion 520 including an opening 522 with a relief 524, a second attachment portion 526 including an opening 528 with a relief 530, and an intermediate portion 518. The first and second attachment portions 520, 526 allow for a surgeon to insert the bone fasteners into the vertebrae first, thereby, providing a complete view of the patient's spine. Then the surgeon may insert the implants 500, 510 by placing them over the bone fasteners at the reliefs 524, 530 and sliding the bone fasteners into position within the openings 522, 528. Once the bone fasteners are in place along the openings 522, 528, additional bone fasteners may be inserted to secure the implants 500, 510 to the vertebrae. The intermediate portions 518 may be reinforced with an absorbable biomaterial that is resorbed over time and as the biomaterial is absorbed, the stiffness of the dynamic spinal fixation systems changes. Referring now to FIG. 33, the multi-component implant 510 allows for some adjustment in length of the intermediate portion 518 along the long axis of the implant 510.

Figure 35:
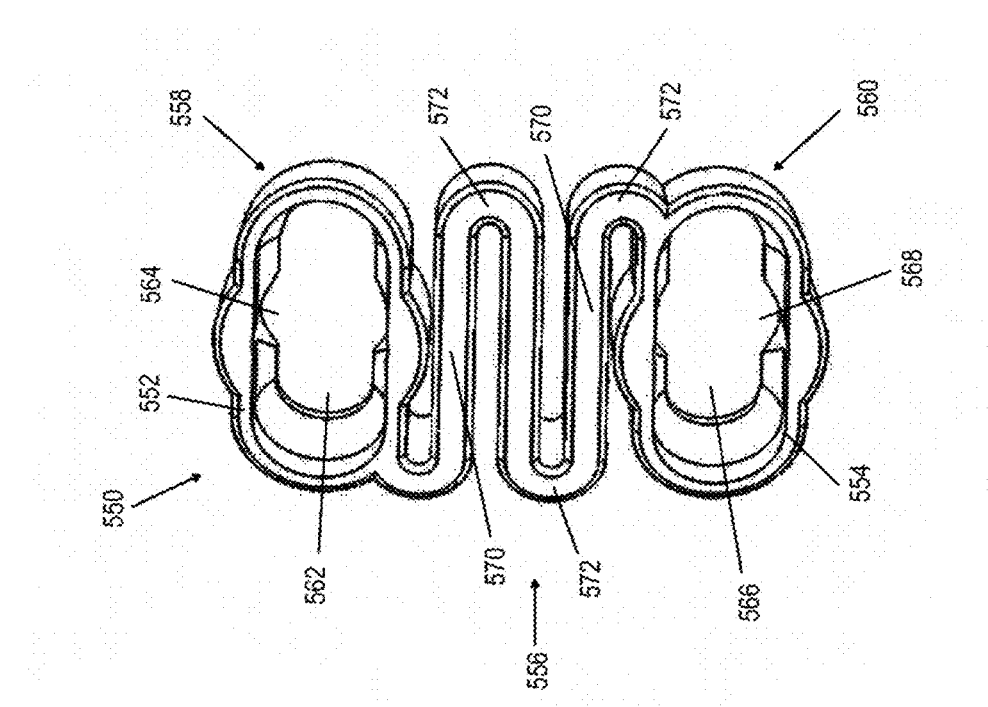
FIG. 35 is a perspective view of the dynamic spinal fixation system embodiment of FIG. 34, in accordance with an aspect of the present invention.
Figure 34:
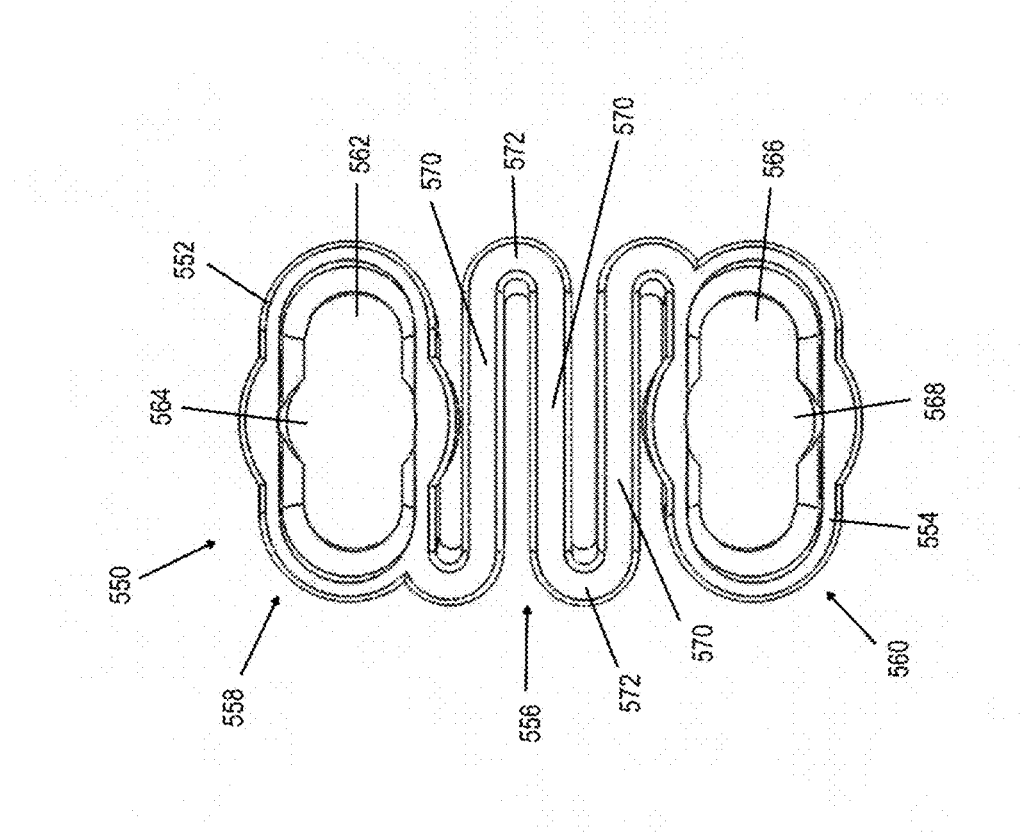
FIG. 34 is a front view of a further embodiment of a dynamic spinal fixation system with attachment portions including openings with reliefs, in accordance with an aspect of the present invention.

Referring now to FIGS. 34 and 35, another dynamic spinal fixation system or plate 550 embodiment is shown. The system 550 includes a first attachment portion 552, a second attachment portion 554, and an intermediate portion 556 that connects the first attachment portion 552 and second attachment portion 554. The intermediate portion 556 may be of the type described above with reference to FIG. 2 and include an elastic mechanism composed of a plurality of straight portions 570 and a plurality of curved portions 572. The first attachment portion 552 is at a superior end 558 of the system 550 and the second attachment portion 554 is at an inferior end 560. The first attachment portion 552 includes a first opening or slot 562 which is oriented in a transverse direction and further includes a relief 564 or a larger aperture creating a "key hole" slot. Likewise, second attachment portion 554 includes a second opening or slot 566 which is oriented in a transverse direction and further includes a relief 568 or larger aperture creating a "key hole" slot. The reliefs 564, 568 are centered in the first and second openings 562, 566, respectively. In alternative embodiments, the openings 562, 566 could also include additional reliefs allowing for additional bone fasteners to be inserted into the vertebrae before placement of the system 550 onto a patient's spine. In other alternative embodiments, the openings 562, 566 could also be oriented vertically or in any other direction. Multiple openings or tracks 562, 566 in each attachment portion 552, 554 may also be included in alternative embodiments.

The reliefs 564, 568 allow the first attachment portion 552 and second attachment portion 554 to be placed over the bone fastener heads, such as screw heads, that are already fixed to a vertebral body. The bone fasteners could also be pins, wires, nails, or any other method for fixing system 550 to a bone. The first and second openings 562, 566 are smaller than the geometry of the head of the bone fastener and the reliefs 564, 568. Thus, the geometry of the first and second openings 562, 566, respectively, allows the first and second attachment portions 552, 554 to be captured between the bone fastener heads and the underlying vertebra when the system 550 is slid into position between the head of the bone fasteners and the vertebra. Once the system 550 is in a desired position the surgeon may insert additional bone fasteners to secure the system 550 to the patient's spine.

Figure 37:
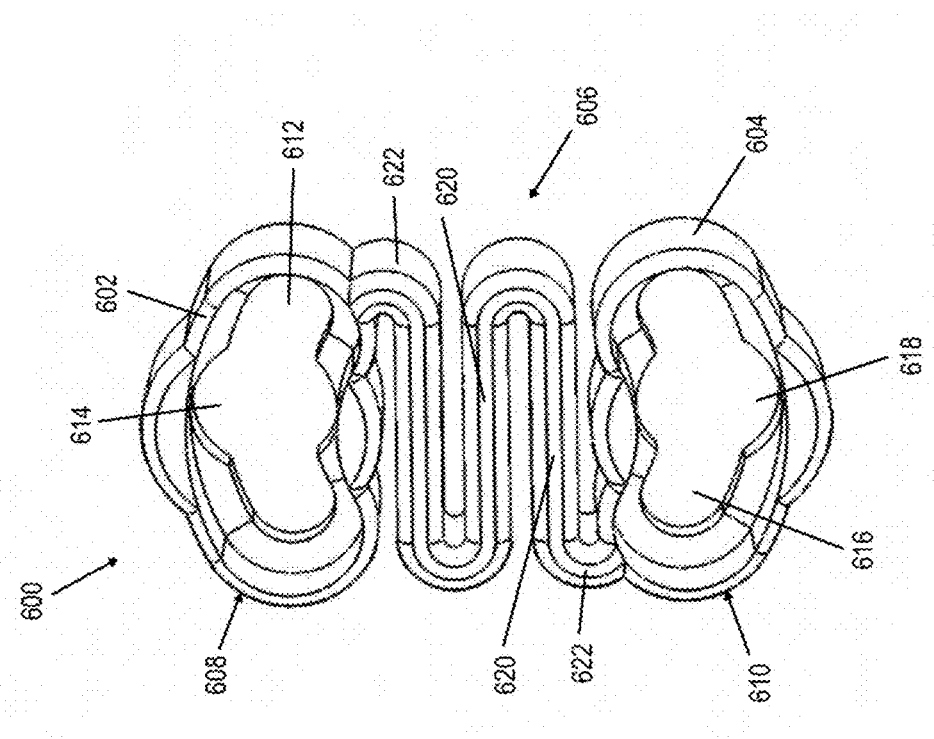
FIG. 37 is a perspective view of the dynamic spinal fixation system embodiment of FIG. 36, in accordance with an aspect of the present invention.
Figure 36:
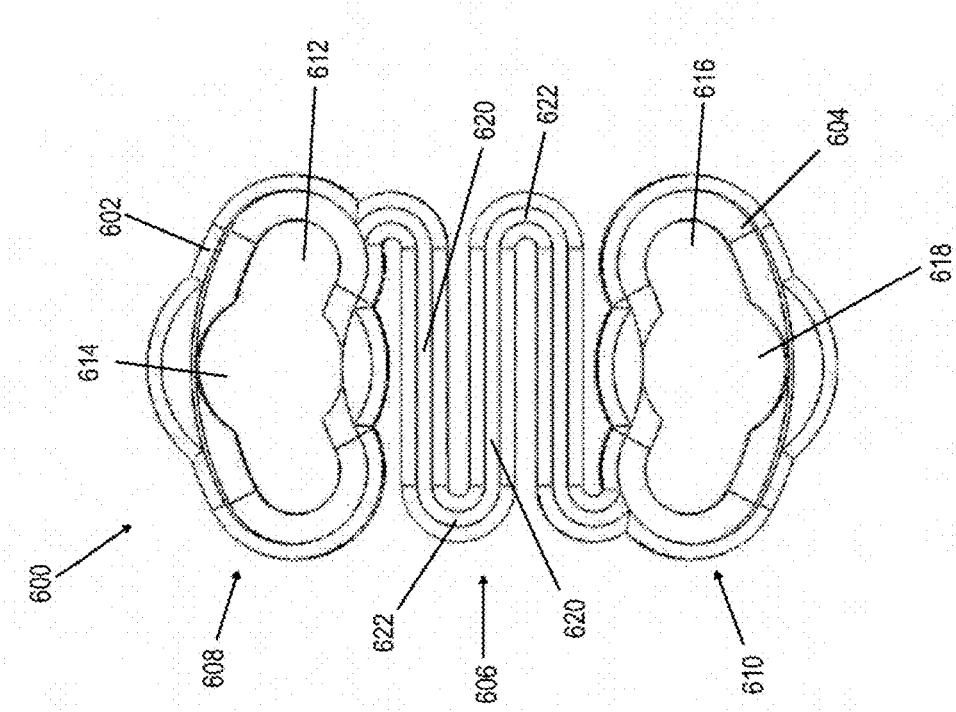
FIG. 36 is a front view of yet another embodiment of a dynamic spinal fixation system with curved attachment portions including openings with reliefs, in accordance with an aspect of the present invention.

An alternative embodiment dynamic spinal fixation system 600 is depicted in FIGS. 36 and 37. The system 600 includes a first attachment portion 602, a second attachment portion 604, and an intermediate portion 606 that connects the first attachment portion 602 and second attachment portion 604. The intermediate portion 606 may be of the type described above with reference to FIG. 2 and include a single elastic mechanism that includes a plurality of straight portions 620 and a plurality of curved portions 622. The first attachment portion 602 is at a superior end 608 of the system 600 and the second attachment portion 604 is at an inferior end 610. The first attachment portion 602 includes a first opening or slot 612 which is curved and further includes a relief or a single larger aperture 614. Likewise, second attachment portion 604 includes a second opening or slot 616 which is curved and further includes a relief or single larger aperture 618. The openings 612, 616 could also include additional reliefs allowing for additional bone fasteners to be inserted into the vertebrae before placement of the system 600 onto a patient's spine. The openings 612, 616 of system 600 are concave slots that may be used to compress the intermediate portion 606 as the system 600 is slid transversely under the already-placed one or more screws or fasteners. Alternatively, the concave slots of openings 612, 616 may be used to distract the intermediate portion 606 or to maintain the same distance between the vertebrae based on the position the fasteners are inserted into the vertebrae. The slots 624 could also be convex allowing the motion segment to be distracted. The system 600 may be inserted onto the spine as described above with reference to FIGS. 34 and 35, however rather than sliding the system into position, the surgeon would rotate the system 600 into position between the head of the bone fasteners and the vertebra.

The dynamic spinal fixation systems of FIGS. 38-39 depict embodiments similar to those described above with reference to FIGS. 34-35, but wherein the systems include alternative relief positions. The reliefs may be located superiorly or inferiorly to the openings of the attachment portions to facilitate compression or distraction of the dynamic spinal fixation systems.

Referring now to FIG. 38, the dynamic spinal fixation system 650 includes first attachment portion 652, second attachment portion 654, and intermediate portion 556 which connects first attachment portion 652 and second attachment portion 654. The first attachment portion 652 is at a superior end 656 of the system 650 and the second attachment portion 654 is at an inferior end 658. The first attachment portion 652 includes a first opening 660 which is oriented in a transverse direction and further includes a relief 662 positioned superior to a midline of the first opening 660. The second attachment portion 654 includes a second opening 664 which is oriented in a transverse direction and further includes a relief 666 positioned inferior to a midline of the second opening 664. The relief 660 is connected to the first opening 660 and the relief 666 is connected to the second opening 664.

Referring now to FIG. 39, the dynamic spinal fixation system 670 includes first attachment portion 672, second attachment portion 674, and intermediate portion 676 which connects first attachment portion 672 and second attachment portion 674. The first attachment portion 672 is at a superior end 678 of the system 670 and the second attachment portion 674 is at an inferior end 680. The first attachment portion 672 includes a first opening 682 which is oriented in a transverse direction and further includes a relief 684 positioned inferior to a midline of the first opening 682. The second attachment portion 674 includes a second opening 686 which is oriented in a transverse direction and further includes a relief 688 positioned superior to a midline of the second opening 686. The relief 684 is connected to the first opening 682 and the relief 688 is connected to the second opening 686.

In the embodiments depicted in FIGS. 34-45, at least one of the attachment portions contains at least one relief allowing a bone fastener head to pass through the dynamic spinal fixation systems. Alternatively, more than one attachment portion may have a relief allowing a bone fastener to pass through the dynamic spinal fixation systems. Further, all the attachment portions could have reliefs allowing bone fasteners to pass through the dynamic spinal fixation systems. The intermediate portions of FIGS. 34-45 may be reinforced with an absorbable biomaterial that is resorbed over time and as the biomaterial is absorbed, the stiffness of the dynamic spinal fixation systems changes. Although the systems illustrated in FIGS. 34-45 only show one level systems, multiple level systems are also contemplated and these multiple level systems include at least one attachment portion with a relief. In addition, the length of each system shown in FIGS. 34-45 may be adjustable to accommodate the spacing between the already-placed bone fasteners. The systems may also be compressed or extended to allow the already-placed bone fasteners to pass through the reliefs in the attachment portions.

Referring now to FIG. 40, a dynamic spinal fixation system 700 is shown. The system 700 includes a first attachment portion 702, second attachment portion 704, and intermediate portion 706 which connects first attachment portion 702 and second attachment portion 704. The first attachment portion 702 and second attachment portion 704 are of the type described above with reference to first attachment portion 702 and second attachment portion 704 of FIGS. 34-35. The intermediate portion 706 or spring-like elastic section has a non-uniform cross-sectional geometry which facilitates the desired stiffnesses in different bending directions. For example, the thickened lateral cross-sectional geometry 708 selectively increases torsional stiffness without significantly increasing flexion/extension stiffness.

As best seen in FIGS. 41-43, another dynamic spinal fixation system 720 is shown. The system 720 includes a first attachment portion 722, second attachment portion 724, and intermediate portion 726 which connects first attachment portion 722 and second attachment portion 724. The first attachment portion 722 includes a first opening 728 that is oriented in a transverse direction and further includes a relief 732. The second attachment portion 724 includes a second opening 730 that is oriented in a transverse direction and further includes a relief 734. The reliefs 732, 734 are centered in the first and second openings 728, 730, respectively. The intermediate portion 726 includes at least one elastic mechanism with a plurality of straight portions 736 and a plurality of curved portions 738 and at least one support strut 740. The support struts 740 may be lateral to the midline and at different distances from the midline based on the desired rigidity of the intermediate portion 726. The support struts 740 are generally parallel to the curved portions 738 and are located between the straight portions 736. In the depicted embodiment there are four support struts 740.

Referring now to FIG. 41, an opening 742 is created between the curved portions 738 and the support struts 740. In FIG. 42, an opening 744 is created between the curved portions 738 and the support struts 740. The opening 744 is larger than the opening 742 because the support struts 740 are closer to the midline in FIG. 42 than in FIG. 41. Referring now to FIG. 43, an opening 746 is created between the curved portions 738 and the support struts 740. Opening 746 is larger than openings 742 and 744 because the support struts 740 are closer to the midline in FIG. 43 than in either FIG. 41 or 42. The support struts 740 may provide various levels of rigidity by reinforcing the intermediate portion 726. The amount of rigidity which intermediate portion 726 has will be based on the distance the support strut 740 is from the midline or the size of the openings 742, 744, and 746. For example, the system 720 of FIG. 43 will be more rigid than the system of FIG. 42 and both will be more rigid than the system of FIG. 41 because strut 740 in FIG. 43 is closest to the midline creating the largest opening 746 and strut 740 in FIG. 41 is farthest from the midline creating the smallest opening 742. The rigidity may be enhanced as the support struts 740 are moved closer to the midline, in particular in bending and torsion, while still allowing the system 720 to deform elastically.

Figure 45:
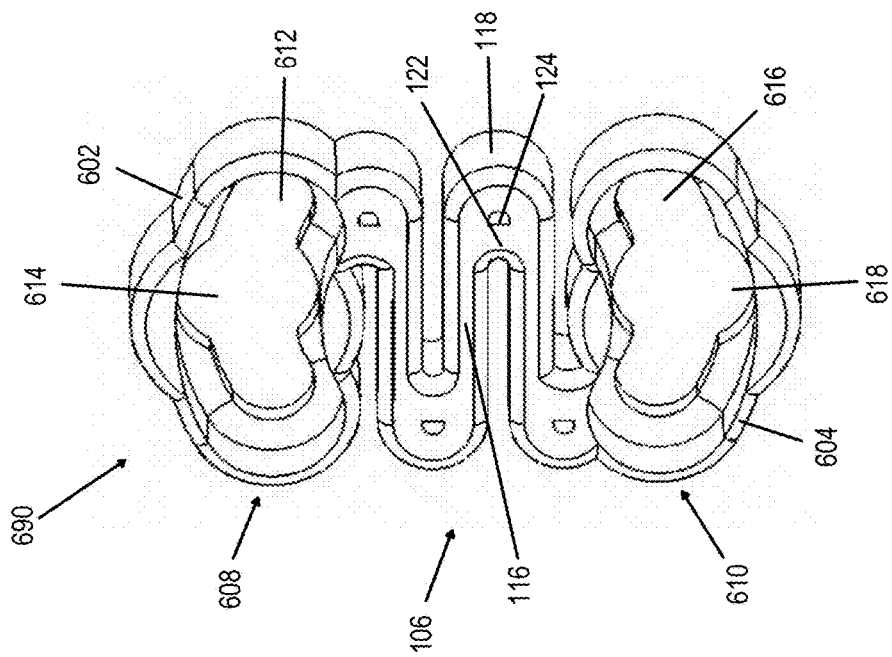
FIG. 45 is a perspective view of the dynamic spinal fixation system embodiment of FIG. 44, in accordance with an aspect of the present invention.
Figure 44:
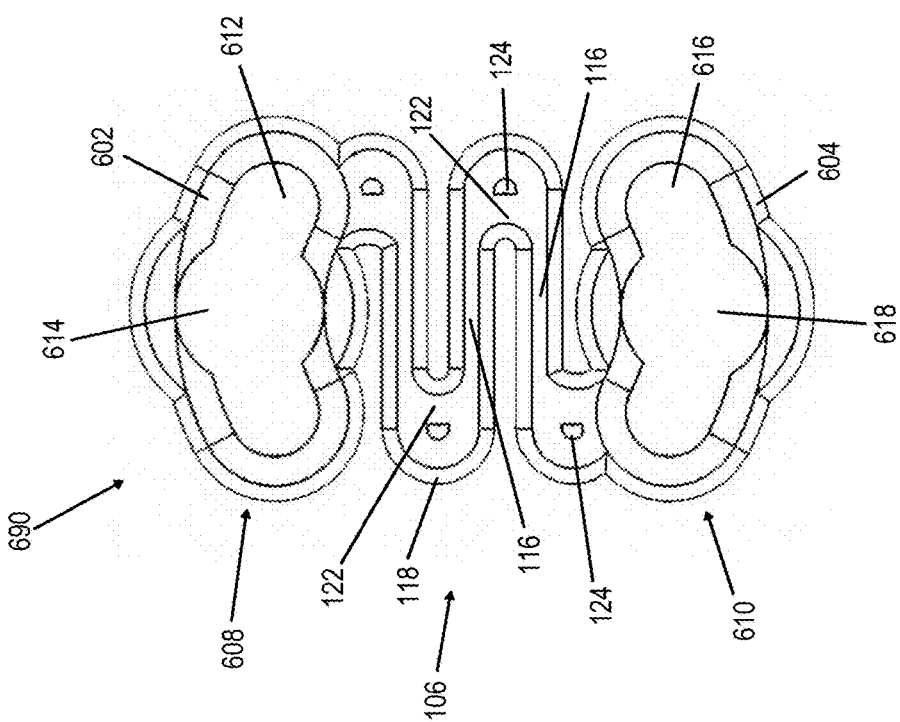
FIG. 44 is a front view of the embodiment dynamic spinal fixation system of FIG. 41 wherein the openings are curved, in accordance with an aspect of the present invention.

FIGS. 44 and 45 illustrate another embodiment of a dynamic spinal fixation system 690. The system 690 includes a first attachment portion 602, a second attachment portion 604, and an intermediate portion 106. The first attachment portion 602 and second attachment portion 604 are of the type described above with reference to FIGS. 36 and 37. The intermediate portion 106 is of the type described above with reference to FIG. 7 wherein the intermediate portion 106 includes at least one support strut 122.

Figure 48:
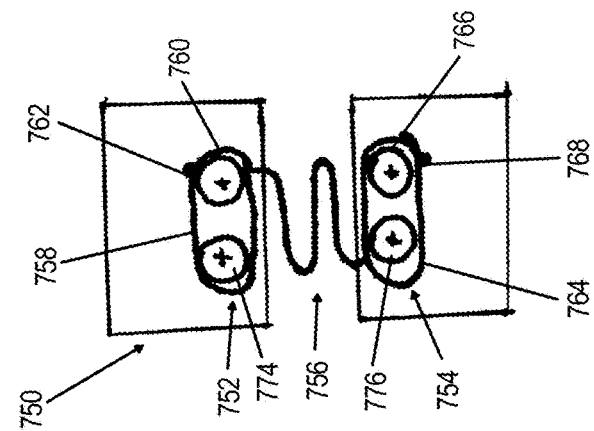
FIG. 48 is a front view of the dynamic spinal fixation system of FIGS. 46 and 47 secured to the two vertebrae with closed arms, in accordance with an aspect of the present invention.
Figure 47:
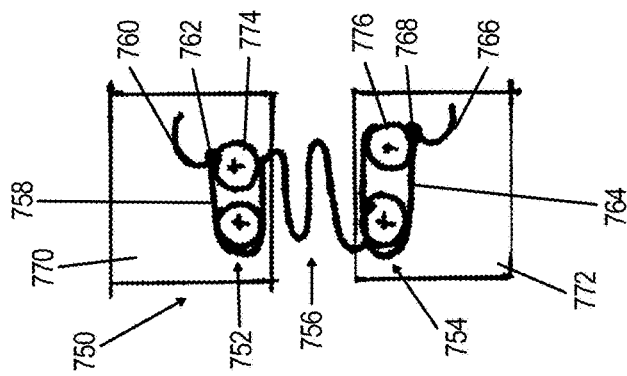
FIG. 47 is a front view of the embodiment of FIG. 46 wherein the dynamic spinal fixation system with attachment portions including openings with reliefs is inserted over the fasteners and the arms are in an open position, in accordance with an aspect of the present invention.
Figure 46:
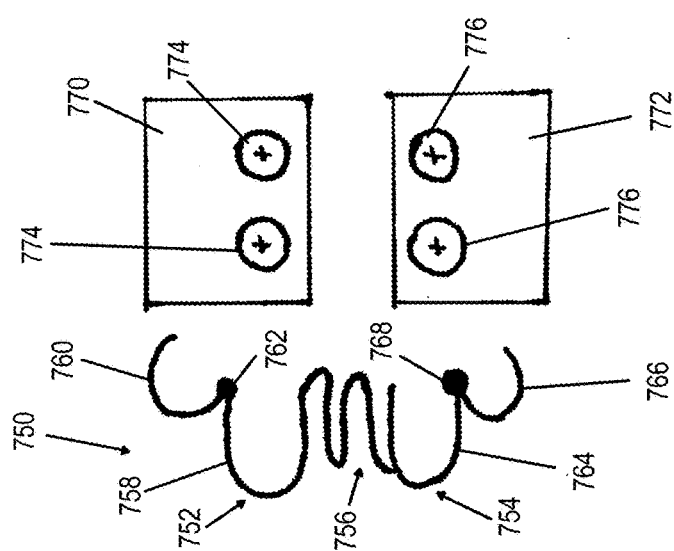
FIG. 46 is an exploded view of another embodiment of a dynamic spinal fixation system with attachment portions including openings with reliefs and two vertebrae with four fasteners secured to the vertebrae, in accordance with an aspect of the present invention.

Referring now to FIGS. 46-48, another embodiment of a dynamic spinal fixation system 750 is shown with a method of inserting the system 750 onto two vertebrae. The system 750 includes a first open attachment portion or platform section 752, a second open attachment portion or platform section 754, and an intermediate portion 756. The intermediate portion 756 may be reinforced with an absorbable biomaterial that is resorbed over time and as the biomaterial is absorbed, the stiffness of the dynamic spinal fixation systems changes. The first open attachment portion 752 and second open attachment portion 754 are open on at least one side. The first open attachment portion 752 includes a base 758, an arm 760, and a hinge mechanism 762 which connects the arm 760 to the base 758 and allows for the arm 760 to open and close. The second open attachment portion 754 includes a base 764, an arm 766, and a hinge mechanism 768 which connects the arm 766 to the base 764 and allows for the arm 760 to open and close. The system 750 may be secured to a first vertebra 770 and a second vertebra 772 by first inserting bone fasteners 774 into the first vertebra 770 and inserting bone fasteners 776 into the second vertebra 772. The bone fasteners 774, 776 are screws in the depicted embodiment, but may also be nails, staples, wires, pins, and the like. Next the arms 760 and 766 are placed in an open position and base 758 is aligned with fasteners 774 and base 764 is aligned with fasteners 776. The system 750 may then be slid laterally between the already inserted bone fasteners 774 and 776 and the first and second vertebrae 770 and 772, respectively. The arms 760 and 766 may then be lowered to close the first attachment portion 752 and the second attachment portion 754 using the hinge mechanisms 762, 768 or similar mechanism. When the arms 760 and 766 have been lowered, the bone fasteners 774 and 776 are captured within the first open attachment portion 752 and second open attachment portion 754, respectively. Bone fasteners 774 and 776 may then be tightened to secure the system 750 to the first and second vertebrae 770 and 772, respectively.

Figure 49:
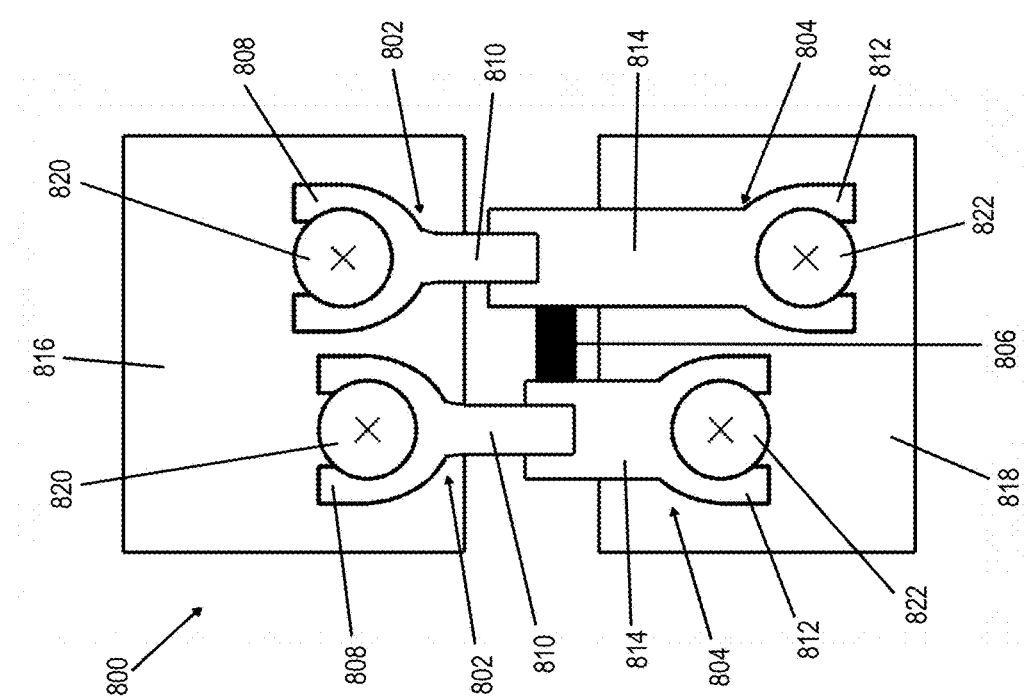
FIG. 49 is a front view of another embodiment dynamic spinal fixation system with curved attachment portions secured to two vertebrae, in accordance with an aspect of the present invention.

Another dynamic spinal fixation system 800 is shown in FIG. 49. The system 800 includes two first attachment portions 802, two second attachment portions 804, and at least one brace 806. The first attachment portions 802 include first attachment sections 808 and first strut portions 810. The second attachment portions 804 include second attachment sections 812 and second strut portions 814. The first strut portions 810 of the two first attachment portions 802 are connected vertically to the second strut portions 814 of the two second attachment portions 804. The strut portions 810 and 814 include a mechanism that has an adjustable length. The attachment portions 802 and 804 have a generally u-shaped geometry that are open on the outside allowing the attachment portions 802 and 804 to be slid between bone fastener heads and the vertebrae. The attachment portions 802 are slid in a superior direction between vertebra 816 and fastener heads 820 to capture the system 800. The attachment portions 804 are slid in an inferior direction between vertebra 818 and fastener heads 822 to capture the system 800. Once attachment portions 802 and 804 are slid into place, although not shown, a hinged enclosure, like the arms 760 and 766 of FIGS. 46-48, may capture the bone fastener heads 820 and 822.

Figure 50:
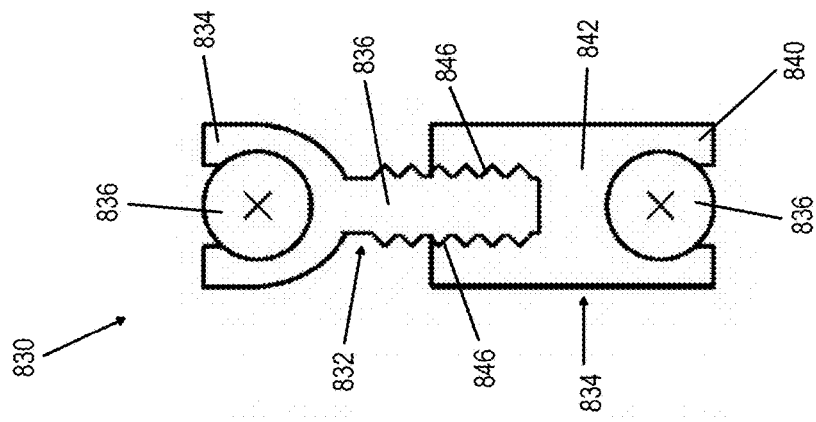
FIG. 50 is a front view of yet another embodiment of a dynamic spinal fixation system with curved attachment portions secured to two vertebrae, in accordance with an aspect of the present invention.

Illustrated in FIG. 50 is another dynamic spinal fixation system 830. The system 830 includes a first attachment portion 832, a second attachment portion 834, and two bone fasteners 836. The first attachment portion 832 includes a first attachment section 834 and a first strut portion 836. The second attachment portion 838 includes a second attachment section 840 and a second strut portion 842. The attachment portions 832 and 834 have a generally U-shaped geometry that is open on the outside allowing the attachment portions 832 and 834 to be slid between bone fastener heads 844 and the vertebrae. The attachment portion 832 is slid in a superior direction and the attachment portion 834 is slid in an inferior direction between the vertebrae and bone fastener heads 844 to capture system 830. The strut portions 840 and 842 include a mechanism that has an adjustable length and the first strut portion 836 includes a plurality of teeth 846 to facilitate engagement of an adjustable mechanism. The systems 750, 800, and 830 of FIGS. 46-50 may be reinforced with an absorbable biomaterial that is resorbed over time and as the biomaterial is absorbed, the stiffness of the dynamic spinal fixation systems changes.

Referring now to FIGS. 51-55, a surgical method for implanting a dynamic spinal fixation system is depicted and will now be described. The method utilizes some of the devices, features, aspects, components and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular vertebrae, but such an application is not intended to be limiting and the method described herein may be used or conducted with vertebrae not specifically discussed herein without departing from the spirit and scope of the surgical method.

Assuming the patient has a spinal injury, disease, or trauma, an anterior spinal surgery, such as an anterior cervical discectomy and fusion ("ACDF"), may be performed to correct the damaged spine using the systems 550 or 600. The methods disclosed each include placing the bone fasteners first and the systems 550 or 600 second. The fasteners may also be used to distract or compress the spine prior to placement of the systems 550 or 600 over the fasteners.

Figure 56:
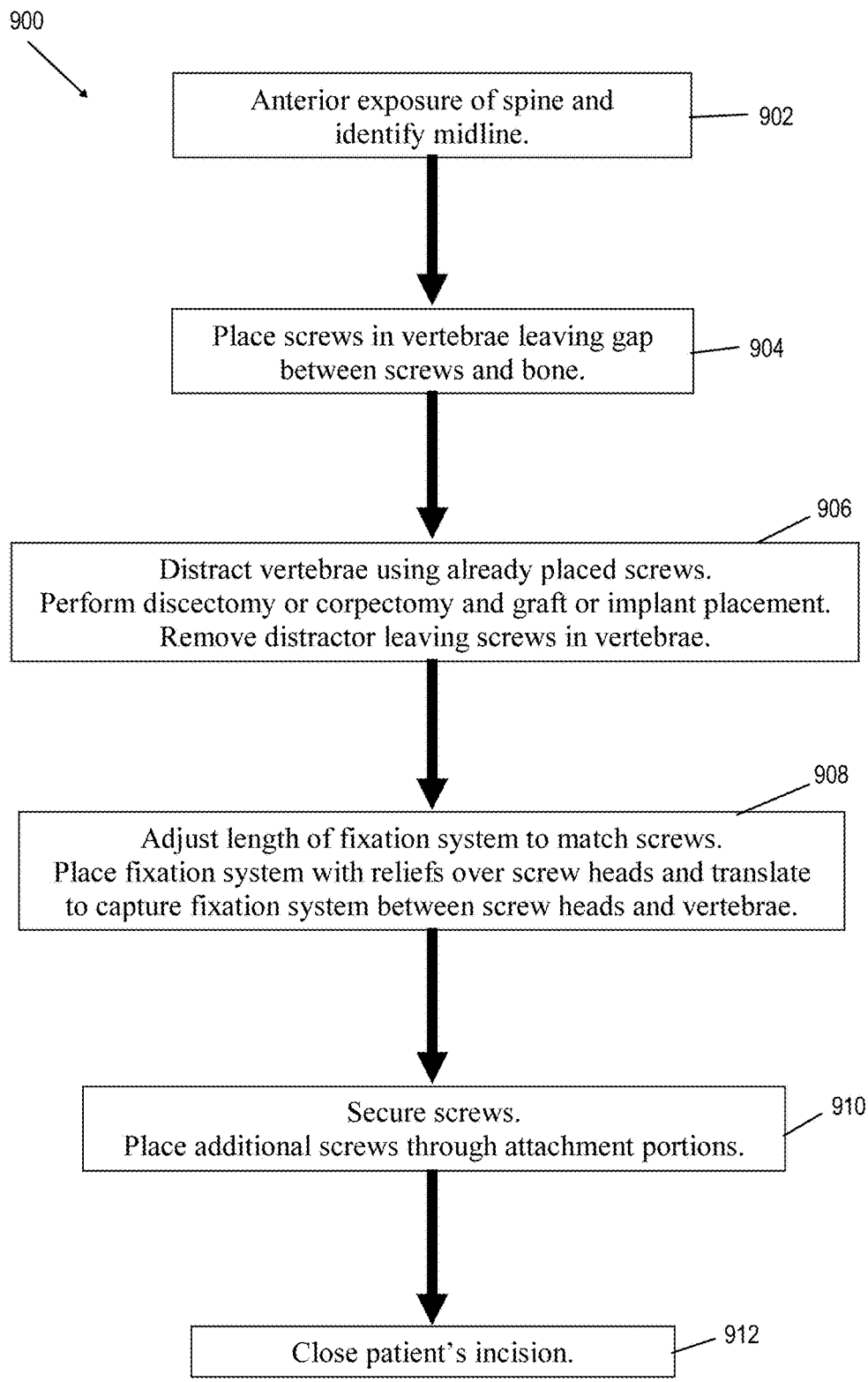
FIG. 56 depicts one embodiment of a surgical method for implanting a dynamic spinal fixation system into a patient's body, in accordance with an aspect of the present invention.

As depicted in FIG. 56, the method 900 consists of the following steps. First, in order to correct a damaged spine an anterior or lateral portion of the spine is exposed by a surgeon, the vertebral level is determined, and the midline position is identified 902. The bone fasteners, screws in the depicted embodiments, are then applied at the superior vertebra and the inferior most vertebrae leaving a gap between the screws and the vertebrae 904. A discectomy or corpectomy is then performed by inserting a distractor into the screws for distraction and once decompression is complete a graft, implant, or interbody spacer is placed into the disc space and then the distraction apparatus is removed 906. Next a system of a desired length is chosen to correspond to the distance between the screws and if compression or distraction is desired, a smaller or larger system is selected. Alternatively, the length of the system may be adjusted by compressing or distracting the system prior to placing the reliefs over the screw heads and translating the system to capture the attachment portions between the screw heads and vertebrae 908. The screws are then tightened to secure the attachment portions between the screw heads and vertebrae with additional screws being inserted through the openings 910 if necessary. Finally, the patient's incision is closed 912.

When a dynamic spinal fixation system is chosen for step 908 the inter-screw distance must first be determined. Then a surgeon must decide whether it is desirable to apply compression or extension to the graft. If the surgeon wishes to apply compression to the graft then a shorter system 550 or 600 is utilized or the system 550 or 600 may be stretched or expanded prior to placing it over the screws. Alternatively, if the surgeon wants to apply distraction to the graft then a longer system 550 or 600 is utilized or the system 550 or 600 may be compressed prior to placing it over the screws.

Figure 52:
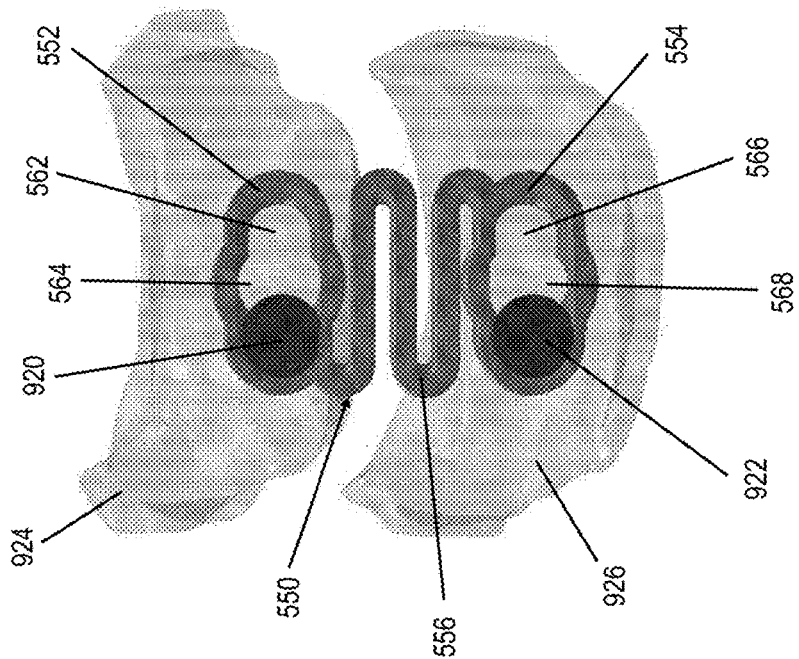
FIG. 52 is a front view of the dynamic spinal fixation system of FIG. 51 after sliding the fixation system along the openings to secure the fasteners, in accordance with an aspect of the present invention.
Figure 51:
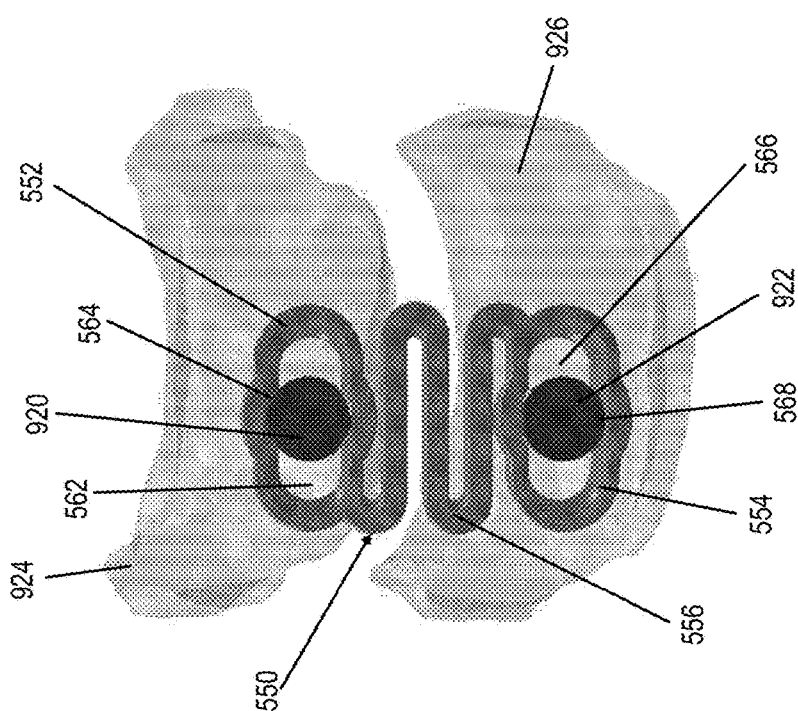
FIG. 51 is a front view of the dynamic spinal fixation system of FIGS. 34 and 35 with the reliefs of the fixation system mating with two aligned fasteners secured to two vertebrae, in accordance with an aspect of the present invention.

As illustrated in FIGS. 51-52, in step 904, a first fastener 920 may be applied to the superior vertebra 924 approximately 2 to 3 millimeters ("mm") off the midline to the right or left side. A second fastener 922 is then applied to the inferior most vertebrae 926 just off the midline, approximately 2 to 3 mm, and on the same side as the first fastener 920. The first vertebra may be adjacent the second vertebra. Alternatively, the first vertebra may be separated from the second vertebra, for example, the first vertebra may be the C4 and the second vertebra may be the C6 in a two level procedure. In the depicted embodiment, the first and second fasteners 920, 922 are applied to the left side of the midline of the vertebrae 924, 926. The reliefs 564, 568 of dynamic spinal fixation system 550 are aligned with the already placed fasteners 920, 922. The system 550 is then slid in line with the midline of the spine and the fasteners 920, 922 move into the left lateral sides of the openings 562, 566, respectively. After the system 550 is positioned, additional fasteners may be applied on the right lateral sides of the openings 562, 566. The fasteners may then be locked to the system 550 by a locking mechanism, such as an expansion screw or an interference type plate or screw. The first and second fasteners 920, 922 may also be applied to the right side of the midline of the vertebrae 924, 926 and then the fasteners 920, 922 would be slid to the right lateral sides of the openings 562, 566, respectively.

Figure 54:
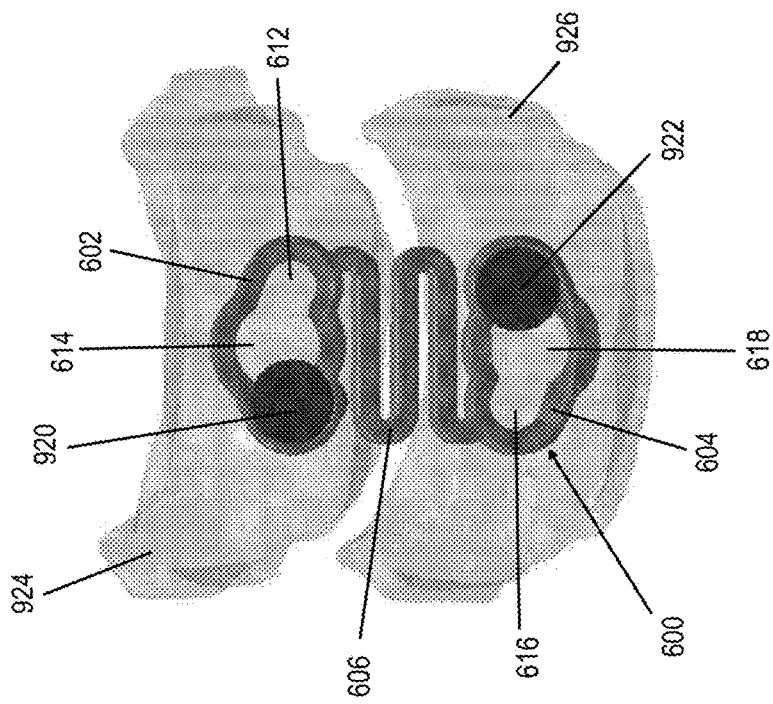
FIG. 54 is a front view of the dynamic spinal fixation system of FIG. 53 after rotation of the fixation system, in accordance with an aspect of the present invention.
Figure 53:
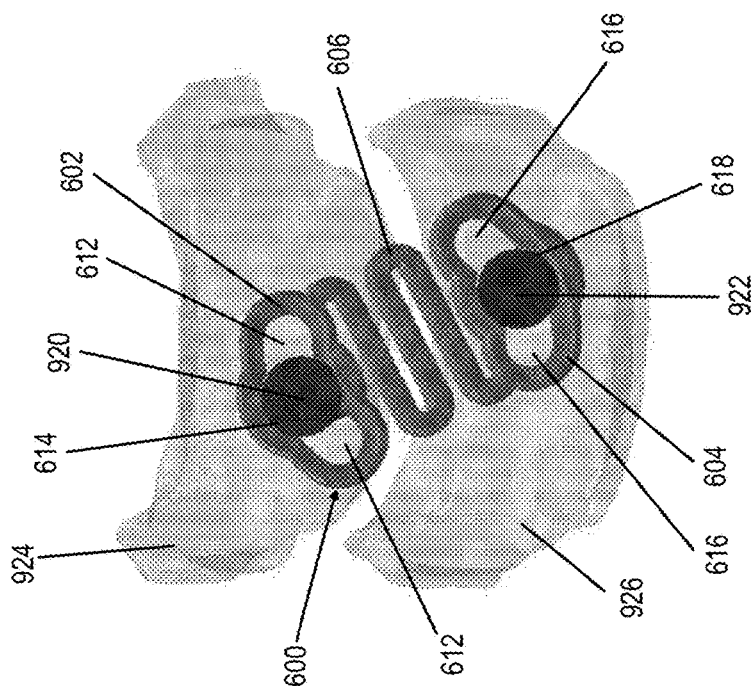
FIG. 53 is a front view of the dynamic spinal fixation system of FIGS. 36 and 37 with the reliefs of the fixation system mating with two offset fasteners secured to two vertebrae, in accordance with an aspect of the present invention.
Figure 55:
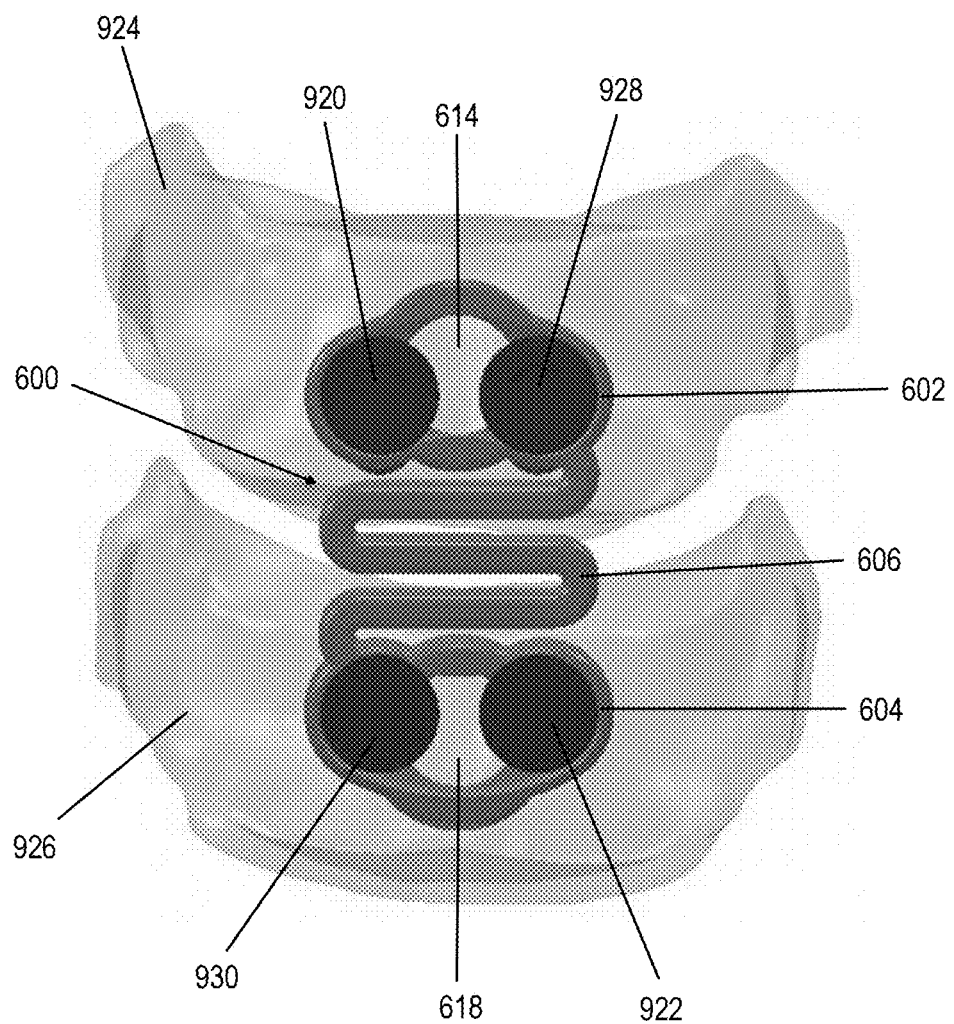
FIG. 55 is a front view of the dynamic spinal fixation system embodiment of FIGS. 53 and 54 secured to two vertebrae with four fasteners, in accordance with an aspect of the present invention.

As illustrated in FIGS. 53-55, in step 904, a first fastener 920 may be applied to the superior vertebra 924 approximately 2 to 3 mm off the midline to the right or left side. A second fastener 922 is then applied to the inferior most vertebrae 926 just off the midline, approximately 2 to 3 mm, and on the side opposite the first fastener 920. The first vertebra may be adjacent the second vertebra. Alternatively, the first vertebra may be separated from the second vertebra, for example, the first vertebra may be the C4 and the second vertebra may be the C6 in a two level procedure. In the depicted embodiment the first fastener 920 is applied to the left side of the midline of the vertebra 924 and the second fastener 922 is applied to the right side of the midline of the vertebra 926. Alternatively, the first fastener 920 may be applied to the right side of the midline of the vertebra 924 and the second fastener 922 may be applied to the left side of the midline of the vertebra 926. In still another alternative embodiment, the first and second fasteners 920 and 922 may be aligned parallel in the vertebrae 924 and 926, respectively.

Once the fasteners 920, 922 are inserted into the vertebrae 924, 926, a dynamic spinal fixation system 600 is aligned at an angle with the first fastener 920 and the second fastener 922 so that the previously placed fasteners 920 and 922 are accommodated at the reliefs 614 and 618 in the first attachment portion 602 and the second attachment portion 604, respectively. The openings 612 and 616 are curved and concave with respect to the center of the system 600. The curved and concave openings 612 and 616 allow the system 600 to be rotated once the system 600 is placed over at least one of the already placed fasteners 920 and/or 922. The system 600 is then rotated in line with the midline of the spine and the fasteners 920 and 922 move into the openings 612 and 616, as best illustrated in FIG. 52. As the system 600 is rotated the radius of curvature of the openings 612 and 616 allows for compression or distraction of the intermediate portion 606 when the system 600 is rotated under the fasteners 920 and 922.

In an alternative embodiment, the first and second fasteners 920, 922 may be applied to the vertebrae 924, 926 parallel to each other. The system 600 is aligned parallel with the fasteners 920, 922 and the reliefs 614 and 618 are aligned with the fasteners 920, 922. Then system 600 is slid into position moving the fasteners 920, 922 into the openings 612, 616.

Once the system 600 is rotated to the desired position along the spine, the first attachment portion 602 and second attachment portion 604 are captured between the heads of the fasteners 920 and 922 and the superior vertebra 924 and inferior vertebrae 926. A third fastener 928 may optionally be inserted into the opening 612 and a fourth fastener 930 may also optionally be inserted into the opening 616 to further secure the system 600 to the first and second vertebrae 924 and 926, respectively. In alternative embodiments, the openings 612 and 616 may also be convex with respect to the center of the system 600 and thereby allow for compression of the intermediate portion 606 when the system 600 is slid laterally under at least one fastener. Although the method has been described with inserting the fasteners in a given sequence, it is understood by one skilled in the art that the fasteners may be inserted into the spine in any sequence and that the dynamic spinal fixation systems may be slide or rotated in either direction.

While the above detailed description of the invention is in the context of the cervical spine, it is understood by one skilled in the art that the same design is scalable for use in the lumbar spine for anterior lumbar interbody fusion ("ALIF") or dynamic stabilization of the cervical and lumbar spine. Further while the preferred and alternative embodiments are comprised of a metallic material, it is understood that the same design is achievable through use of an elastic, hyperelastic, or deformable polymer, ceramic, or composite.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:
1. A spinal fixation system, comprising:
 a member with a superior end and an inferior end comprising:
  a first attachment portion at the superior end, wherein the first attachment portion includes a first bone fastener opening;
  a second attachment portion at the inferior end, wherein the second attachment portion includes a second bone fastener opening; and an intermediate portion connecting the first attachment portion and the second attachment portion, wherein the intermediate portion comprises:
a third attachment portion with a third opening;
a first elastic mechanism connecting the first attachment portion and the third attachment portion; and
a second elastic mechanism connecting the third attachment portion and the second attachment portion.

2. The spinal fixation system of claim 1, wherein the member is asymmetrical across the sagittal plane, the member is asymmetrical across the transverse plane, and the member is asymmetrical across the coronal plane.

3. The spinal fixation system of claim 1, wherein the intermediate portion is an elastic mechanism and wherein the elastic mechanism includes a plurality of curved sections and straight sections, wherein the curved sections are connected to the straight sections.

4. The spinal fixation system of claim 3, wherein the straight sections are transverse to the sagittal plane.

5. The spinal fixation system of claim 3, wherein the cross-section of the elastic mechanism in the sagittal plane is selected from polygonal in the sagittal plane and oblong in the sagittal plane.

6. The spinal fixation system of claim 3, wherein the intermediate portion includes at least one support strut.

7. The spinal fixation system of claim 6, wherein a position of the at least one support strut is selected from lateral to a midline of the member and aligned along the midline of the member.

8. The spinal fixation system of claim 6, wherein the at least one support strut is positioned adjacent to at least one of the plurality of curved sections forming an opening between the at least one support strut and at least one of the plurality of curved sections.

9. The spinal fixation system of claim 3, wherein the member further comprises:
at least one stop member positioned between two adjacent sections of the elastic mechanism.

10. The spinal fixation system of claim 9, wherein the at least one stop member is positioned between two adjacent straight sections of the elastic mechanism.

11. The spinal fixation system of claim 10, wherein the at least one stop member includes a first portion to stop movement of the elastic mechanism along a superior-inferior axis.

12. The spinal fixation system of claim 10, wherein the at least one stop member includes a first portion attached adjacent to a second portion and wherein the first portion mates with the second portion to inhibit movement of the elastic mechanism along a superior-inferior axis.

13. The spinal fixation system of claim 3, further comprising:
an interbody fusion cage device coupled to the intermediate portion.

14. The spinal fixation system of claim 1, further comprising:
a relief in at least one of the first bone fastener opening and the second bone fastener opening.

15. The spinal fixation system of claim 1, wherein the first bone fastener opening has a first relief and the second bone fastener opening has a second relief.

16. The spinal fixation system of claim 15, wherein the position of the first relief is selected from centered in the first bone fastener opening, superiorly in the first bone fastener opening, and inferiorly in the first bone fastener opening and the position of the second relief is selected from centered in the second bone fastener opening, superiorly in the second bone fastener opening, and inferiorly in the second bone fastener opening.

17. The spinal fixation system of claim 15, wherein the first relief of the first attachment portion is sized to receive a first bone fastener and the second relief of the second attachment portion is sized to receive a second bone fastener.

18. The spinal fixation system of claim 15, wherein the first bone fastener opening and the second bone fastener opening are curved in the coronal plane along a midline of the member.

19. The spinal fixation system of claim 1, wherein the member is curved in the sagittal plane to correspond to the shape of a patient's spine and in the transverse plane to correspond to the shape of the patient's vertebrae.

* * * * *